US006800435B2

(12) United States Patent
Soderlund et al.

(10) Patent No.: US 6,800,435 B2
(45) Date of Patent: Oct. 5, 2004

(54) INSECT SODIUM CHANNELS FROM INSECTICIDE-SUSCEPTIBLE AND INSECTICIDE-RESISTANT HOUSE FLIES

(75) Inventors: David M. Soderlund, Geneva, NY (US); Douglas C. Knipple, Geneva, NY (US); Patricia J. Ingles, Geneva, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 85 days.

(21) Appl. No.: 09/428,371

(22) Filed: Oct. 28, 1999

(65) Prior Publication Data

US 2003/0096336 A1 May 22, 2003

Related U.S. Application Data

(60) Division of application No. 08/772,512, filed on Dec. 24, 1996, now Pat. No. 6,022,705, which is a continuation-in-part of application No. 08/608,618, filed on Mar. 1, 1996, now abandoned.

(51) Int. Cl.[7] .................. C12Q 1/68; C12P 21/06; C12N 15/87; C07H 21/02; C07H 21/04
(52) U.S. Cl. .................. 435/6; 435/465; 435/69.1; 435/455; 536/23.1; 536/23.5
(58) Field of Search .................. 435/6, 69.1, 465, 435/455, 458, 172.3, 70.1, 252.3, 254.11, 320.1, 348, 91.1; 536/23.1, 23.5; 514/1, 2, 44

(56) References Cited

U.S. PATENT DOCUMENTS

| 5,593,862 A | 1/1997 | Hall et al. |
| 5,593,864 A | 1/1997 | Arena et al. .................. 435/69.1 |

FOREIGN PATENT DOCUMENTS

| EP | 0 615 976 A1 | 9/1994 |
| WO | WO 96/14860 | 5/1996 |
| WO | WO 96/15220 | 5/1996 |

OTHER PUBLICATIONS

Pihl–Carey, K. BioWorld Today. vol. 10, pp.1–2 (1999).*
Crooke, S. Antisense Res. and Application. pp.1–50. (Ed. by S. Crooke, Springer–Verlag publishers, 1999).*
Branch, A. Trends in Biochem. Sci. vol. 23, pp. 45–50 (1998).*
Palu, G. et al, J. Biotech. vol. 68, pp. 1–13 (1999).*
Agrawal, S. et al. Molecular Med. Today. vol. 6, pp. 72–81 (2000).*
Tamm, I. et al. The Lancet, vol. 358, pp. 489–497 (2001).*
Williamson et al., "Identification of Mutations in the Housefly *Para*–type Sodium Channel Gene Associated with Knockdown Resistance (kdr) to Pyrethroid Insecticides," *Mol. Gen. Genet.*, 252:51–60 (1996).
Miyazaki et al., "Cloning and Sequencing the *Para*–type Sodium Channel Gene From Susceptible and *Kdr*–resistant German Cockroaches (*Blattella germanica*) and House Fly (*Musca Domestica*)," *Mol. Gen. Genet.*, 252:61–68 (1996).

Doyle et al., "PCR–Based Phylogenetic Walking: Isolation of *Para*–Homologous Sodium Channel Gene Sequences From Seven Insect Species and an Arachnid," *Insect Biochem.*, 21:689–696 (1991).
Williamson et al., "Knockdown Resistance (kdr) to DDT and Pyrethroid Insecticides Maps to a Sodium Channel Gene Locus In the Housefly (*Musca Domestica*)," *Mol. Gen. Genet.*, 240:17–22 (1993).
Knipple et al., "Tight Genetic Linkage Between the *kdr* Insecticide Resistance Trait and a Voltage–Sensitive Sodium Channel Gene in the House Fly," *Proc. Natl. Acad. Sci. USA*, 91:2483–2487 (1994).
Ingles et al., "Characterization of Sodium Channel Genes from Insecticide–Susceptible and Insecticide–Resistant House Flies," Abstracts for the Society of Neuroscience, 21:1824, Abstract 717.11 (1995).
Ingles et al., "Characterization of Voltage–Sensitive Sodium Channel Gene Coding Sequences from Insecticide–Susceptible and Knockdown–Resistant House Fly Strains," *Insect Biochem, Molec. Biol.*, 26:319–326 (1996).
Feng, G., et al., Cell 82:1001–1011 (1995).
Knipple, D.C., et al., Proc Natl Acad Sci USA 91:2483–2487 (1994).
Knipple, D.C., et al., Arch Insect Biochem Physiol 16:45–53 (1991).
Loughney, K., et al., Cell 58:1143–1154 (1989).
Noda, M., et al., Nature 312:121–127 (1984).
Noda, M., et al Nature 320: 188–192 (1986).
O'Dowd, D.K., et al., J. Neurosci 15:4005–4012 (1995).
Soderlund, D.M. and Bloomquist, J.R. Annu Rev Entomol 34:77–96 (1989).
Soderlund, D.M. and Bloomquist, J.R. In *Pesticide Resistance in Arthropods* (Edited by R.T. Roush and B.E. Tabashnik), pp. 58–96. Chapman and Hall, New York, NY (1990).
Soderlund, D.M., and Knipple, D.C., in *Molecular Action of Insecticides on Ion Channels*, eds. Clark, J.M., American Chemical Society, Washington, D.C., pp. 97–108 (1994).
Stuhmer, W., Methods in Enzymology 207:319–339 (1992).
Terlau, H., et al. FEBS Letters 293:93–96 (1991).
Thackeray, J.R. and Ganetzky, B., J. Neurosci 14:2569–2578 (1994).

(List continued on next page.)

*Primary Examiner*—Ram R. Shukla
*Assistant Examiner*—Jane Zara
(74) *Attorney, Agent, or Firm*—Nixon Peabody LLP

(57) ABSTRACT

The present invention is directed to isolated nucleic acid molecules encoding a voltage-sensitive sodium channel (VSSC) of *Musca domestica*, the VSSC being capable of conferring insecticide susceptibility or insecticide resistance to *Musca domestica*, as well as to the isolated voltage-sensitive sodium channels of *Musca domestica* encoded thereby. Nucleic acid molecules encoding insecticide susceptible VSSCs and nucleic acid molecules encoding insecticide resistant VSSCs are provided. Methods for increasing or decreasing the expression of functional voltage-sensitive sodium channels in host cells are also provided, as well as methods using the sodium channels. Also provided is a method for isolating other voltage-sensitive sodium channels.

18 Claims, 7 Drawing Sheets

OTHER PUBLICATIONS

Thackeray, J.R. and Ganetzky, B., Genetics 141:203–214 (1995).
Williamson, M.S., et al., Mol Gen Genet 240:17–22 (1993).
Auld, V.J., et al. Proc Natl Acad Sci USA 87:323–327 (1990).
Bloomquist, J.R., and Soderlund, D.M., Mol Pharmacol 33:543–550 (1988).
Ingles, P.J., et al., Soc Neurosci Abst 21:1824 1995.
Kontis, K.J., Goldin, A.L., Mol Pharmacol 43:635–644 (1993).
Moran, O., et al., Biochem Biophys Res Comm 202:1438–1444 (1994).
Noda, M., et al., FEBS Letters 259:213–216 (1989).
Pusch, M., et al., Eur Biophys J 20:127–133 (1991).
Salkoff, L., et al., Science 237:744–749 (1987).
EMBL Accession No. MD38813 (May 10, 1996).
EMBL Accession No. MD38814 (May 10, 1996).
SWALL Accession No. Q25439 (Nov. 1, 1996).
SWALL Accession No. Q25440 (Nov. 1, 1996).
EMBL Accession No. MDPARA (Sep. 17, 1996).
SWALL Accession No. Q94615 (Feb. 1, 1997).
Smith et al.,"The L1014F Point Mutation in the House Vascl Sodium Channel Confers Knockdown Resistance to Pyrethroids," *Insect Biochem. Molec. Biol.* 27(10):807–812 (1997).
Martinez–Torres et al., "Molecular Studies of Knockdown Resistance to Pyrethroids: Cloning of Domain II Sodium Channel Gene Sequences from Insects," *Pesticide Science* 51(3):265–270 (1997).
Warmke et al., "Functional Expression of *Drosophila para* Sodium Channels: Modulation by the Membrane Protein TipE and Toxin Pharmacology," *J. General Physiol.* 110(2):119–133 (1997).
Smith et al., "Actions of the Pyrethroid Insectides Cismethrin and Cypermethrin on House Fly *Vascl* Sodium Channels Expressed in *Xenopus oocytes*," *Archives of Insect Biochemistry and Physiology* 38:126–136 (1998).

* cited by examiner

```
NAIDM   MTEDSDSISEEERSLFRPFTRESLLQIEQRIA.EHEKQKELERKRAAEGE..........QIRYDDEDEDEGPQPDPTLEQGVPIPVRMQ  79
538ge   ------------------------------L-----------------.........--------A-------------------M-  79
para    ------------------------------V----------------A-.-----VPRYGRKKKQKE-----------------L-  90
                                                                                            IS2
        GSFPPELASTPLEDIDPFYSNVLTFVVISKGKDIFRFSASKAMMLLDPFNPIRRVAIYILVHPLFSLFIITTILTNCILMIMPTTPTVESTEVIFTGIYT  179
        ----F---------------I------------------L------------------------T-----------------------------------  179
        ----Y---------------V------------------M-------------------------V----------------------------------  190
                        IS3                                              IS4                    IS5
        FESAVKVMARGFILCPFTYLRDAWMWLDFVVIALAYVTMGIDLGNLAALRTFRVLRALKTVAIVPGLKTIVGAVIESVKNLRDVIILIMFSLSVFALMGL  279
        ──────────                                                                                          279
                 #      IS6                                #                                               290
        QIYMGVLTQKCIKRFPLDGSWGNLTDENWFLHNSNSNWFTENDGESYPVCGNVSGAGQCCGEDYVCLQGFGPNPNYDYTSFDSFGWAFLSAFRLMTQDFW  379
        ---Q---R-----------------FL--S------FT-ND-E-Y-V----V-----GE-----------D-----------------------------  379
        ---E---K-----------------DY--R------YS-DE-I-F-L----I-----DD-----------G-----------------------------  390
                                                                                                      IP
        EDLYQHVLQAAGPWMHLFFIVIIFLGSFYLVNLILAIVAMSYDELQKKAEEEEAAEEEAIREAEEAAAAKAAKLEERANVAAQAAQDAADAAAAALHPEM 479
        ---H--Q-----------------------------------------------K-----------------------VA----Q---D-AA-------- 479
        ---L--R-----------------------------------------------R-----------------------AQ------A---A-EE----- 490
                                                        *                                          *
        AKSPTYSCISYELFVGGEKGNDDNNKEKMSIRSVEVESESVSVIQRQPAPTTAP.ATTKVRKVSTTSLSLPGSPFNLRRGSRSSHKYTIRNGRGRFGIPGS 578
        ----------------------------------------------P.-------------------L------------------------------- 578
        ---------------------------------------------HQ--------------I------------------------------------- 590
```

```
                                                                                    *
SYGSHKNRPFKDESHKGSAETIEGEEKRDVSKEDLGLDEELDEEABGDEGQLDGDIIHAQNDDEIIDDYPADCFPDSYYKFPILAGDEDSPFWQGWGN 1277
--------I--------------V-----------------A-GD--Q-----------------QN-DE-I-D-----F--------E-------------- 1277
--------M----A-----------------------------G-CE--P----------------H.-ED-L-E----C----------D-------------- 1258
              IIIS1                                                          IIIS2                                IIIS3
LRLKITFQLIENKYFETAVITMILMSSLALALEDVHLPDRPVMQDILYYMQRIFTVIFFLEMLIKWMLALGFKVYFTNAWCWLDFVIVMLSLINLVAVWSGL 1377
--------Q-----N----------------D--VM---------------F---------------------------L-------L--VWS-L 1377
--------R----D----------------Q--IL-----------------L-----------V--F--SLV-A 1358
           IIIS4                                                               IIIS5              #                                          #
NDIAVFRSMRTLRALRPLRAVSRWEGMKVVVNALVQAIPSIFNVLLVCLIFWLIFAIMGVQLFAGKYFKCKDGNDTVLSHEIIPNRNACKSENYIWENSA 1477
---ND-AV--RS-----------V--WE--K---------------------------------------------K-G-D-V----------K------E---- 1477
---GG--QA--KT----------M--MQ--R---------------------------------------------E-M-G-K----------E---V---- 1458
       IIIP                                                 IIIS6
MNFDHVGNAYLCLFQVATFKGWIQIMNDAIDSREVDKQPIRETNIYMYLYFVFFIIRGSFFTLNLFIGVIIDNFNEQKKKAGGSLEMFMTEDQKKYYNAM 1577
-----------------------------------------------------------------------------------------------N--- 1577
-----------------------------------------------------------------------------------------------S--- 1558
         IVS1                                                                   IVS2                              IVS3
KKMGSKKPLKAIPRPRWRPQAIVFEIVTDKKFDIIIMLFIGINMFTMTLDRYDASEAYNNVLDKLNGIFVVIFSGECLLKIFALRYHYFKEPWNLFDVVV 1677
---------------------------EA--N---K--G-----------------------G--------------K------- 1677
------------------------------DT--A--Y--A-----------S-------------------I---------- 1658
```

```
                                    IVS4                                              IVS5
        VILSIIGLVLSDIIEKYFVSPTLLRVVRVAKVGRVLRLVKGAKGIRTLLFFALAMSLPALFNICLLLFLVMFIFAIFGMSFFMHVKEKSGINAVYNFKTFG 1777
        ---------------------------------------------------------------------------------------A-------- 1777
        ---------------------------------------------------------------------------------------D-------- 1758

IVP                                                    #       IVS6
        QSMILLFQMSTSAGMDGVLDAINEEDCDPPDNDKGYPGNCGSSATVGITFLLSYLVISFLIVIMYIAVILENYSQATEDVQEGLTDDDYDMYYEIWQQF 1877
        ---------------------------------------------------------------------D-------------------------- 1877
        ---------------------------------------------------------------------A-------------------------- 1858

DPEGTQYIRYDQLSEFLDVLEPPLQIHKPNKYKIISMDMPICRGDMMYCVDILDALTKDFFARKGNPIEETGEIGEIAARPDTEGYDPVSSTLWRQREEY 1977
        ---------------------------M-------------------------------------------D------------------------ 1977
        ---------------------------I-L-----------------------------------------E------------------------ 1958
                                                                              ◆       ◆            ◆
                                                                                                   ◆
        CAKLIQNAWRRYK.......NGPPQEGDEGEAAGGEDGAEGGEGEGSSGGGDDGGSATGATAAAGAT..SPSDPDAGEADGASVG...GPLSPGCV 2063
        --K---N---RY-.......NGPPQE--E-EAAG-EDGAEGGEGEGSSG--GDDDG-S-T.....AGAT..SPTDPD-GE-DG-SAGNGG-PLSP-CV 2062
        --R---H---KH-ARGEGGGSFEPDTDH--G-DPDA-DPAPDEATDGDAPA--DGSVN-T-E--AD-DESNVNSPGEDAAAA-AA-AA-AAA-TTTA-SP 2055
                          *                                           ◆        ◆             ◆

SGGSNGRQTAVLVESDGFVTKNGHKVVIHSRSPSITSRTADV 2105
        ---------------------------------------- 2104
        SG-------------------------------------- 2100
        GA--A-----------------------------------
```

INSECT SODIUM CHANNELS FROM INSECTICIDE-SUSCEPTIBLE AND INSECTICIDE-RESISTANT HOUSE FLIES

This application is a divisional application of Ser. No. 08/772,512, filed on Dec. 24, 1996, now U.S. Pat. No. 6,022,705, issued on Feb. 8, 2000, which is a continuation-in-part of U.S. Ser. No. 08/608,618, filed Mar. 1, 1996, abandoned, the contents of which are hereby incorporated by reference.

The subject matter of this application was made with support from the United States Government under USDA Grant No. 94-37302-0408.

FIELD OF THE INVENTION

The present invention relates generally to insect sodium channel proteins, and more particularly to insecticide-susceptible and insecticide-resistant voltage-sensitive sodium channels of the house fly *Musca domestica*.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

Cell membranes must allow passage of various polar molecules, including ions, sugars, amino acids, and nucleotides. Special membrane proteins are responsible for transferring such molecules across cell membranes. These proteins, referred to as membrane transport proteins, occur in many forms and in all types of biological membranes. Each protein is specific in that it transports a particular class of molecules (such as ions, sugars, or amino acids) and often only certain molecular species of the class. All membrane transport proteins that have been studied in detail have been found to be multipass transmembrane proteins. By forming a continuous protein pathway across the membrane, these proteins enable the specific molecules to cross the membrane without coming into direct contact with the hydrophobic interior of the lipid bilayer of the plasma membrane.

There are two major classes of membrane transport proteins: carrier proteins and channel proteins. Carrier proteins bind the specific molecule to be transported and undergo a series of conformational changes in order to transfer the bound molecule across he membrane. Channel proteins, on the other hand, need not bind the molecule. Instead, they form hydrophilic pores that extend across the lipid bilayer; when these pores are open, they allow specific molecules (usually inorganic ions of appropriate size and charge) to pass through them and thereby cross the membrane. Transport through channel proteins occurs at a much faster rate than transport mediated by carrier proteins.

Channel proteins which are concerned specifically with inorganic ion transport are referred to as ion channels, and include ion channels for sodium, potassium, calcium, and chloride ions. Ion channels which open in response to a change in the voltage across the membrane are referred to as voltage-sensitive ion channels.

The sodium channel is one of the most thoroughly characterized of the voltage-sensitive channels (see FIG. 1 for a model of a voltage-sensitive sodium channel). In vertebrates, sodium channels in the brain, muscle, and other tissues are large membrane glycoprotein complexes composed of an alpha subunit (230–270 kDa) and 1–2 tightly associated smaller (33–38 kDa) beta subunits (reviewed by Catterall 1992). The large alpha subunit forms the ion permeable pore while the smaller subunits play key roles in the regulation of channel function (Isom et al. 1992; reviewed by Isom et al. 1994). The alpha subunit is common to purified channel preparations from *Electrophorus electricus* (electric eel) electric organ (Noda et al. 1984), rat brain (Noda et al. 1986), rat skeletal muscle (Barchi 1988) and chick heart muscle (Catterall 1986). Other studies have revealed the existence of multiple closely related isoforms of the sodium channel found in different animal species, in different tissues within the same species, and even in the same tissue (Catterall et al. 1981; Frelin et al. 1984; Rogart 1986; Moczydlowski et al. 1986).

The structure of invertebrate sodium channels is not as well defined. Gene cloning studies have established the existence of alpha subunits of structure similar to those described for vertebrates (Loughney et al. 1989; Ramaswami and Tanouye 1989; Okamoto et al. 1987). Analysis of the para behavioral mutant (paralytic; Suzuki et al. 1971) of *Drosophila melanogaster* revealed that the para gene encodes a Drosophila sodium channel alpha subunit (Loughney et al. 1989). The entire para cDNA sequence was determined (Loughney et al. 1989; Thackeray and Ganetzky 1994).

The kdr mutant of the house fly *Musca domestica* has also been studied. The kdr insecticide resistance trait of the house fly confers reduced neuronal sensitivity to the rapid paralytic and lethal actions of DDT and pyrethroid insecticides (Soderlund and Bloomquist 1990). Because these insecticides are known to modify neuronal excitability by altering the inactivation kinetics of voltage-sensitive sodium channels (Soderlund and Bloomquist 1989; Bloomquist 1993), efforts to identify the molecular basis of kdr resistance have focused on the pharmacology and structure of this target.

Recently, tight genetic linkage between the kdr trait and a restriction fragment length polymorphism located within a segment of the house fly homolog of the para gene of *Drosophila melanogaster* was demonstrated (Knipple et al. 1994). Similar linkage studies have also documented tight linkage of the super-kdr resistance trait of the house fly (Williamson et al. 1993) to molecular markers lying within the para-homologous voltage-sensitive sodium channel gene.

Elucidation of the structure of the house fly sodium channel gene will enable the screening of potential insecticidal agents which act upon the sodium channel.

A need continues to exist, therefore, for the determination of the primary structure of the house fly sodium channel, i.e. the nucleotide and amino acid sequences of the channel.

SUMMARY OF INVENTION

To this end, the subject invention provides the 6318 nucleotide coding sequence (SEQ ID NO:1) of the voltage-sensitive sodium channel gene from insecticide-susceptible (NAIDM strain) house flies (*Musca domestica*), determined by automated direct DNA sequencing of PCR fragments obtained by amplification on first strand cDNA from adult heads. The deduced 2105-residue amino acid sequence (SEQ ID NO:3) exhibits overall structure and organization typical of sodium channel alpha subunit genes and is 90.0% identical to that of the *D. melanogaster* para gene product. There is no evidence for the existence of multiple splice variants among voltage-sensitive sodium channel cDNAs obtained from adult house fly head preparations. Comparison of the coding sequence of the voltage-sensitive sodium channel gene of the kdr insecticide-resistant house fly strain (538ge strain) to that of the NAIDM strain reveals 12 amino acid differences in the 538ge strain. The amino acid sequence (SEQ ID NO:4) of the Kdr strain is only 2104 residues in length, as a result of five (5) amino acid substitutions, four (4) amino acid deletions, and three (3) amino acid insertions as compared to the 2105-residue amino acid sequence (SEQ ID NO:3) of the NAIDM strain. The nucleotide sequence (SEQ ID NO:2) of the Kdr strain is therefore 6315 nucleotides in length, which is three nucleotides shorter than the nucleotide sequence (SEQ ID NO:1) of the NAIDM strain.

More particularly, the subject invention provides an isolated nucleic acid molecule encoding a voltage-sensitive sodium channel of *Musca domestica*, wherein the voltage-sensitive sodium channel is capable of conferring sensitivity or resistance to an insecticide in *Musca domestica*. In one embodiment, the nucleic acid molecule confers insecticide susceptibility to the house fly, and in another embodiment the nucleic acid molecule confers insecticide resistance to the house fly. The nucleic acid molecule conferring insecticide resistance is preferably a mutated form of the nucleic acid molecule encoding the insecticide susceptible channel. The invention also provides an antisense nucleic acid molecule complementary to mRNA encoding the voltage-sensitive sodium channel of *Musca domestica*.

The isolated nucleic acid molecules of the invention can be inserted into suitable expression vectors and/or host cells. Expression of the nucleic acid molecules encoding the sodium channels results in production of functional sodium channels in a host cell. Expression of the antisense nucleic acid molecules or fragments thereof in a host cell results in decreased expression of the functional sodium channels.

The invention further provides a ribozyme having a recognition sequence complementary to a portion of mRNA encoding a voltage-sensitive sodium channel of *Musca domestica*. The ribozyme can be introduced into a cell to also achieve decreased expression of sodium channels in the cell.

The invention further provides a method of screening a chemical agent for the ability of the chemical agent to modify sodium channel function, and a method of obtaining DNA encoding a voltage-sensitive sodium channel of *Musca domestica*.

Further provided is an isolated nucleic acid molecule encoding a voltage-sensitive sodium channel of an insect, wherein the nucleic acid molecule encodes a first amino acid sequence having at least 95% amino acid identity to a second amino acid sequence. The second amino acid sequence is, in two preferred embodiments, SEQ ID NO:3 or SEQ ID NO:4.

The invention also provides an isolated voltage-sensitive sodium channel of *Musca domestica*, and antibodies or antibody fragments specific for the sodium channel. The antibodies or antibody fragments can be used to detect the presence of the sodium channel in samples.

Further provided is an isolated voltage-sensitive sodium channel of *Musca domestica*, wherein the voltage-sensitive sodium channel is comprised of a protein having a first amino acid sequence with at least 95% amino acid identity to a second amino acid sequence. In two preferred embodiments, the second amino acid sequence is SEQ ID NO:3 or SEQ ID NO:4.

Also provided by the subject invention is a plasmid designated pPJI1 and deposited with the ATCC under Accession No. 97831, as well as a KpnI/AatII restriction fragment of about 3620 bp of the plasmid designated pPJI1. Further provided is a plasmid designated pPJI2 and deposited with the ATCC under Accession No. 97832, as well as an AatII/SphII restriction fragment of about 2700 bp of the plasmid designated pPJI2. When the above two restriction fragments are ligated together at their AatII sites, the resulting nucleic acid molecule encodes a voltage-sensitive sodium channel which confers susceptibility to an insecticide in *Musca domestica*. This resulting nucleic acid molecule is also provided by the subject invention.

BRIEF DESCRIPTION OF THE DRAWINGS

These and other features and advantages of this invention will be evident from the following detailed description of preferred embodiments when read in conjunction with the accompanying drawings in which:

FIG. 3 shows the alignment of the predicted amino acid sequences of $Vssc1^{NAIDM}$ (NAIDM) (SEQ ID NO:3) and $Vssc1^{538ge}$ (538ge) (SEQ ID NO:4) with that of the $a^+b^-c^-d^+e^-f^-h^-i^+$ splice variant of the *D. melanogaster* para sequence (para) obtained using the DNASTAR computer program (Clustal method). Residues that are identical to the NAIDM sequence in both 538ge and para are indicated as dashes (–) in the latter two sequences; gaps introduced to obtain optimal alignment are indicated as periods (.). The locations of 24 putative helical transmembrane domains (e.g., IS1, IS2, etc.) and four putative pore-forming domains (e.g., IP, IIP) are marked by solid bars above the NAIDM sequence. Also marked above the NAIDM sequence are possible sites for N-linked glycosylation (#) cAMP-dependent protein kinase phosphorylation (*), and protein kinase C phosphorylation (●)

DETAILED DESCRIPTION

Figure 1:
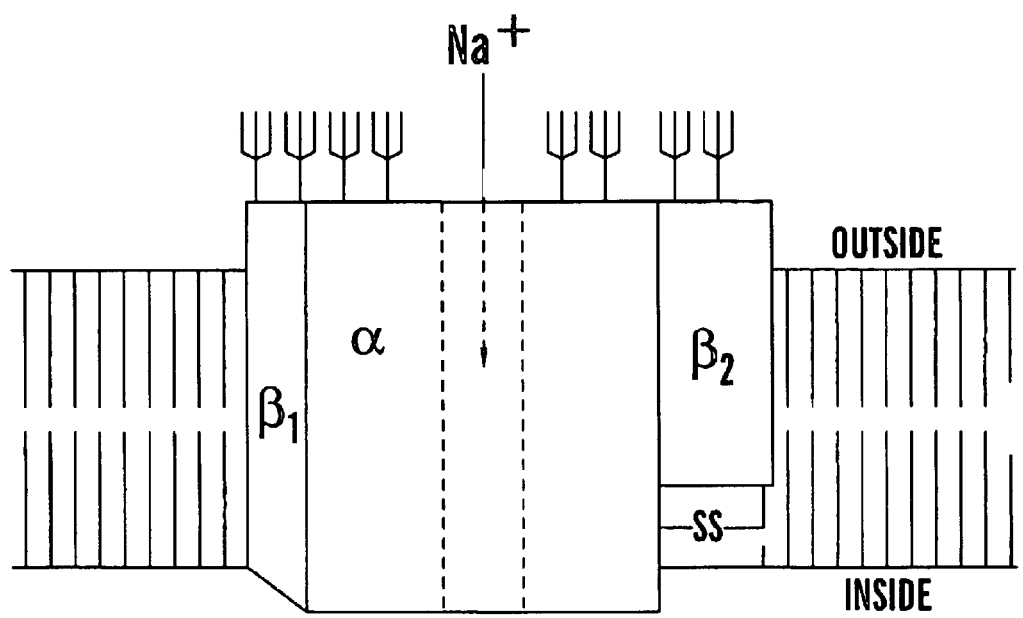
FIG. 1 is a model of a voltage sensitive sodium channel from mammalian brain in the plasma membrane. The alpha and $beta_1$ subunits interact noncovalently; the alpha and $beta_2$ subunits are linked by disulfide bonds. The branched structures at the outer surface of the channel represent oligosaccharides.

The plasmids designated pPJI1 and pPJI2 have each been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md., 20852 under ATCC Accession No. 97831 (pPJI1) and ATCC Accession No. 97832 (pPJI2). Both deposits were made on Dec. 20, 1996.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized nucleic acid molecules). The term "isolated" when used in conjunction with a channel refers to a channel encoded by such an "isolated" nucleic acid molecule, generally expressed in a membrane, such as a plasma membrane within a cell or a synthetic lipid bilayer membrane. The expressed "isolated" channel has the pharmacological properties of a functional sodium channel.

As further used herein, the terms "corresponding to" or "having" or "as shown in" when used in conjunction with a SEQ ID NO for a nucleotide sequence refer to a nucleotide sequence which is substantially the same nucleotide sequence, or derivatives or equivalents thereof (such as deletion and hybrid variants thereof, splice variants thereof, etc.). Nucleotide additions, deletions, and/or substitutions, such as those which do not affect the translation of the DNA molecule, are within the scope of a nucleotide sequence corresponding to or having or as shown in a particular nucleotide sequence (i.e. the amino acid sequence encoded thereby remains the same). Such additions, deletions, and/or substitutions can be, for example, point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting VSSC. Similarly, the term "corresponding to" or "having" or "as shown in" when used in conjunction with a SEQ ID NO for an amino acid sequence refers to an amino acid sequence which is substantially the same amino acid sequence or derivatives or equivalents thereof. Amino acid additions, deletions, and/or substitutions which do not negate the ability of the resulting protein to form a functional sodium channel are within the scope of an amino acid sequence corresponding to or having or as shown in a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. As used herein, two amino acid residues are conservative substitutions of one another where the two residues are of the same type. In this regard, for purposes of the present invention, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residues, which include histidine, lysine, and arginine. Leucine, isoleucine, valine, and methionine all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French and Robson 1983, Taylor 1986, and Bordo and Argos 1991.

As further used herein, the term "corresponding to" or "having" or "as shown in" or "consisting of" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotides or amino acids within the recited sequence. For example, those skilled in the art will readily understand that an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

The function of the encoded sodium channel can be assayed according to methods known in the art, such as by voltage clamp analysis of the channel following the functional expression of the channel in oocytes of the frog *Xenopus laevis* (see Taglialatela et al. 1992 and Stuhmer 1992 for a general discussion of the voltage clamp analysis of receptors and ion channels expressed in *Xenopus oocytes*). As used herein, "functional expression" refers to the synthesis and any necessary post-translational processing of a sodium channel molecule in a host cell so that the channel is inserted properly in the cell membrane and is capable of conducting sodium ions in response to an experimentally-imposed change in the cell membrane potential or upon exposure to appropriate pharmacological agents.

As further used herein, "sensitivity" and "resistance" refer to the relative responses of genetically-defined insect populations to the paralytic or lethal actions of a test insecticide. For example, a dose of DDT [1,1-bis-(4-chlorophenyl)-2,2, 2-trichloroethane] of approximately 0.02 $\mu$g per adult fly will kill approximately 50 of the treated individuals of a susceptible (Cooper-S) house fly strain, whereas doses of approximately 0.5 $\mu$g per adult fly are required to kill approximately 50% of the treated individuals of a resistant (538ge) house fly strain (Sawicki 1978). The absolute doses that define susceptibility and resistance vary with the insect species and genetically defined populations examined, the test insecticide employed, and the method of exposure. In general, an insect strain or population is considered "resistant" if it exhibits tolerance to a test insecticide (assessed as the dose required to poison 50% of a treated population or group) that is at least 10 times greater than the tolerance of an appropriate reference, or "susceptible" population. Test insecticides include not only DDT but also analogs of DDT (e.g., methoxychlor, perthane) and pyrethroid insecticides (e.g., deltamethrin, fenvalerate, resmethrin, permethrin).

As also used herein, insects include *Musca domestica* (the house fly), the fruit or vinegar fly (*Drosophila melanogaster*), and various other insect species of agricultural, medical or veterinary importance, such as *Heliothis virescens* (the tobacco budworm) *Leptinotarsa decemlineata* (the Colorado potato beetle), *Blattella germanica* (the German cockroach), and *Aedes aegypti* (the yellow fever mosquito).

The subject invention provides an isolated nucleic acid molecule encoding a voltage-sensitive sodium channel (VSSC) of *Musca domestica*, wherein the VSSC is capable of conferring sensitivity or resistance to an insecticide in *Musca domestica*. The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the VSSC.

In one embodiment, the VSSC confers insecticide susceptibility to *Musca domestica*. An example of such an insecticide susceptible VSSC is the channel encoded by the nucleotide sequence as shown in SEQ ID NO:1. SEQ ID NO:1 is the DNA sequence of one allele of the VSSC of *Musca domestica*. The amino acid sequence encoded by this allele is shown in SEQ ID NO:3.

In another embodiment, the VSSC confers insecticide resistance to *Musca domestica*. An example of such an insecticide resistant VSSC is the channel encoded by the nucleotide sequence as shown in SEQ ID NO:2. SEQ ID NO:2 is the DNA sequence of another allele of the VSSC of *Musca domestica* characteristic of the kdr insecticide resistant strain. The amino acid sequence encoded by this mutant allele is shown in SEQ ID NO:4.

The insecticide resistant allele preferably has the nucleotide sequence of a second nucleic acid molecule with one or more mutations therein, wherein the second nucleic acid molecule encodes an insecticide sensitive VSSC and wherein one or more mutations in the second nucleic acid molecule render the resulting VSSC resistant to an insecticide (hence the term "mutant" allele) In one embodiment, the mutant allele (having amino acid SEQ ID NO:4) has the amino acid sequence encoded by the susceptibility allele (amino acid SEQ ID NO:3) with amino acid differences as follows: a substitution of phenylalanine for leucine at amino acid residue 1014 of SEQ ID NO:3; a substitution of isoleucine for methionine at amino acid residue 1140 of SEQ ID NO:3; a substitution of aspartic acid for glycine at amino acid residue 2023 of SEQ ID NO:3; a deletion of amino acid residues 2031–2034 of SEQ ID NO:3 (glycine-alanine-threonine-alanine); a substitution of threonine for serine at amino acid residue 2042 of SEQ ID NO:3; a substitution of alanine for valine at amino acid residue 2054 of SEQ ID NO:3; and an insertion of three amino acid residues (asparagine-glycine-glycine) after amino acid residue 2055 of SEQ ID NO:3 (between amino acid residues 2055 and 2056 of SEQ ID NO:3). One or more of these amino acid differences can be included in an insecticide resistant VSSC. Other suitable sites for mutations can be identified by conventional, molecular genetic approaches, such as the identification of amino acid sequence substitutions/insertions/deletions in the VSSC sequences of other insecticide-resistant house fly strains.

The invention also provides an antisense nucleic acid molecule that is complementary to the mRNA encoding the VSSC, or a fragment thereof. Antisense nucleic acid molecules can be RNA or single-stranded DNA. Antisense molecules can be complementary to the entire DNA molecule encoding the VSSC, i.e. of the same nucleotide length as the entire molecule. It may be desirable, however, to work with a shorter molecule. In this instance, fragments of the entire antisense molecule can be used. Suitable fragments are capable of hybridizing to the mRNA encoding the entire molecule, and preferably consist of at least twenty nucleotides. These antisense molecules and fragments thereof can be used to reduce steady state levels of a VSSC gene product of *Musca domestica*, by introducing into cells an RNA or single-stranded DNA molecule that is complementary to the mRNA of the VSSC (i.e. by introducing an antisense molecule). The antisense molecule can base-pair with the mRNA of the VSSC, preventing translation of the mRNA into protein. Thus, an antisense molecule to the VSSC of *Musca domestica* can prevent translation of mRNA encoding the VSSC into a functional sodium channel protein.

More particularly, an antisense molecule complementary to mRNA encoding a VSSC of *Musca domestica*, or a fragment thereof, can be used to decrease expression of a functional VSSC of *Musca domestica*. A cell with a first level of expression of a functional VSSC of *Musca domestica* is first selected, and then the antisense molecule (or fragment thereof) is introduced into the cell. The antisense molecule (or fragment thereof) blocks expression of functional VSSCs of *Musca domestica*, resulting in a second level of expression of a functional VSSC of *Musca domestica* in the cell. The second level is less than the initial first level.

Antisense molecules can be introduced into cells by any suitable means. Suitable cells include *Xenopus oocytes* which are useful host cells for studying the expression of the encoded sodium channel, and various insect cells, including but not limited to the insect cell lines *Drosophila Schneider* (Johansen et al. 1989), Drosophila $K_c$ (Sang 1981), Sf9 (Smith et al. 1983), and High Five® (see U.S. Pat. No. 5,300,435). In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995.

The invention further provides a special category of antisense RNA molecules, known as ribozymes, having recognition sequences complementary to specific regions of the mRNA encoding the VSSC of *Musca domestica*. Ribozymes not only complex with target sequences via complementary antisense sequences but also catalyze the hydrolysis, or cleavage, of the template mRNA molecule. Examples, which are not intended to be limiting, of suitable regions of the mRNA template to be targeted by ribozymes are any of the regions encoding the 24 putative transmembrane domains of the VSSC of *Musca domestica*.

Expression of a ribozyme in a cell can inhibit gene expression (such as the expression of a VSSC of *Musca domestica*). More particularly, a ribozyme having a recognition sequence complementary to a region of a mRNA encoding a VSSC of *Musca domestica* can be used to decrease expression of a functional VSSC of *Musca domestica*. A cell with a first level of expression of a functional VSSC of *Musca domestica* is first selected, and then the ribozyme is introduced into the cell. The ribozyme in the cell decreases expression of a functional VSSC of *Musca domestica* in the cell, because mRNA encoding the VSSC is cleaved and cannot be translated.

Ribozymes can be introduced into cells by any suitable means. Suitable cells include *Xenopus oocytes* which are useful host cells for studying the expression of the encoded sodium channel, and various insect cells, including but not limited to the insect cell lines *Drosophila Schneider*, Drosophila $K_c$, Sf9, and High Five®. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors (note that the DNA encoding the ribozyme does not need to be "incorporated" into the genome of the host cell; it could be expressed in a host cell infected by a viral vector, with the vector expressing the ribozyme, for instance). For a general discussion of ribozymes and their use, see Sarver et al. 1990, Chrisey et al. 1991, Rossi et al. 1992, and Christoffersen et al. 1995.

The nucleic acid molecules of the subject invention can be expressed in suitable host cells using conventional techniques. Any suitable host and/or vector system can be used to express the VSSCs. These include, but are not limited to, eukaryotic hosts such as mammalian cells (i.e., Hela cells, Cv-1 cells, COS cells), *Xenopus oocytes*, and insect cells (i.e. insect cell lines such as *Drosophila Schneider*, *Drosophila K$_c$*, Sf9, and High Five®).

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, sodium channel expression is often studied in *Xenopus oocytes*. DNA encoding the VSSC can be injected into the oocyte nucleus or transformed into the oocyte using a suitable vector, or mRNA encoding the VSSC can be injected directly into the oocyte, in order to obtain expression of a functional VSSC in the oocyte. It may be beneficial when expressing the sodium channels of the subject invention in *Xenopus oocytes* to coexpress a nucleic acid molecule encoding a tipE protein (Feng et al. 1995). Tip E has been found to be necessary to obtain expression of some sodium channels in *Xenopus oocytes* (Feng et al. 1995).

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the VSSC has been introduced can be used to produce (i.e. to functionally express) the voltage-sensitive sodium channel.

Having identified the nucleic acid molecules encoding VSSCs and methods for expressing functional channels encoded thereby, the invention further provides a method of screening a chemical agent for the ability of the chemical agent to modify sodium channel function. The method comprises introducing a nucleic acid molecule encoding the VSSC into a host cell, and expressing the VSSC encoded by the molecule in the host cell. The expression results in the functional expression of a VSSC in the membrane of the host cell. The cell is then exposed to a chemical agent and evaluated to determine if the chemical agent modifies the function of the VSSC. From this evaluation, chemical agents effective in altering the function of the sodium channel can be found. Such agents may be, for example, tetrodotoxin, veratridine, and scorpion venom toxins. Additional agents can be found in Soderlund and Knipple 1994.

Cells transformed to include the VSSC according to the subject invention can be exposed to various potential insecticides and pesticides and evaluated for their susceptibility to the agents to develop and identify insect control agents that will not cause adverse effects to vertebrate species. Exemplary methods of screening are described in Eldefrawi et al. 1987 and Rauh et al. 1990. The evaluation of the function of the sodium channel can be by any means known in the art. In one embodiment, the evaluation comprises monitoring sodium transport through the VSSC. Sodium transport can be monitored by pre-incubating cells in a medium containing one or more chemical agents, adding a medium containing radiosodium ($^{22}Na^+$), incubating the cells further in this medium, and isolating cells by filtration. Sodium transport is detected by the measurement of $^{22}Na^+$ within the cells by liquid scintillation counting or other radiometric techniques (Bloomquist and Soderlund 1988). Alternatively, [$^{14}C$]guanidinium ion can be employed as the radiotracer in the place of sodium using the same procedure (Jacques et al. 1978). In another embodiment, the function of the VSSC can be evaluated by pre-incubating cells to equilibrium with a sodium-selective fluorescent chelating agent (e.g., SBFI [sodium-binding benzofuran isophthalate]), washing the cells, exposing the cells to a test agent, and monitoring the increase in intracellular sodium by measuring the fluorescence of the SBFI-sodium complex (Deri and Adam-Vizi 1993).

The nucleic acid molecules of the subject invention can be used either as probes or for the design of primers to obtain DNA encoding other VSSCs by either cloning and colony/plaque hybridization or amplification using the polymerase chain reaction (PCR).

Specific probes derived from SEQ ID NOs 1 or 2 can be employed to identify colonies or plaques containing cloned DNA encoding a member of the VSSC family using known methods (see Sambrook et al. 1989). One skilled in the art will recognize that by employing such probes under high stringency conditions (for example, hybridization at 42° C. with 5×SSPC and 50% formamide, washing at 50–65° C. with 0.5×SSPC), sequences having regions which are greater than 90% identical to the probe can be obtained. Sequences with lower percent identity to the probe, which also encode VSSCs, can be obtained by lowering the stringency of hybridization and washing (for example, by reducing the hybridization and wash temperatures or reducing the amount of formamide employed).

More particularly, in one embodiment, the method comprises selection of a DNA molecule encoding a VSSC of an insect, or a fragment thereof, the DNA molecule having a nucleotide sequence selected from the group consisting of SEQ ID NO:1 and SEQ ID NO:2, and designing an oligonucleotide probe for a VSSC based on SEQ ID NO:1 or SEQ ID NO:2. A genomic or cDNA library of an insect is then probed with the oligonucleotide probe, and clones are obtained from the library that are recognized by the oligonucleotide probe so as to obtain DNA encoding another VSSC.

Specific primers derived from SEQ ID NOs 1 or 2 can be used in PCR to amplify a DNA sequence encoding a member of the VSSC family using known methods (see Innis et al. 1990). One skilled in the art will recognize that by employing such primers under high stringency conditions (for example, annealing at 50–60° C., depending on the length and specific nucleotide content of the primers employed), sequences having regions greater than 75% identical to the primers will be amplified.

More particularly, in a further embodiment the method comprises selection of a DNA molecule encoding a VSSC of an insect, or a fragment thereof, the DNA molecule having a nucleotide sequence selected from the group consisting of SEQ ID NO:1 and SEQ ID NO:2, designing degenerate oligonucleotide primers based on regions of SEQ ID NO:1 or SEQ ID NO:2, and employing such primers in the polymerase chain reaction using as a template a DNA sample to be screened for the presence of VSSC-encoding sequences. The resulting PCR products can be isolated and sequenced to identify DNA fragments that encode polypeptide sequences corresponding to the targeted region of a VSSC.

Various modifications of the nucleic acid and amino acid sequences disclosed herein are covered by the subject invention. These varied sequences still encode a functional VSSC. The invention thus further provides an isolated nucleic acid molecule encoding a VSSC of an insect, the nucleic acid molecule encoding a first amino acid sequence having at least 95% amino acid identity to a second amino acid sequence, the second amino acid sequence being as shown in SEQ ID NO:3. The resulting encoded VSSC is susceptible to an insecticide. The invention also provides an isolated nucleic acid molecule encoding a VSSC of an insect, the nucleic acid molecule encoding a first amino acid sequence having at least 95% amino acid identity to a second amino acid sequence, the second amino acid sequence being as shown in SEQ ID NO:4. The resulting VSSC is resistant to an insecticide.

The invention further provides isolated voltage-sensitive sodium channels of *Musca domestica*, wherein the VSSC is capable of conferring sensitivity or resistance to an insecticide in *Musca domestica*. In one embodiment, the VSSC confers susceptibility to an insecticide in *Musca domestica*, such as the VSSC encoded by the nucleotide sequence as shown in SEQ ID NO:1 (which encodes an amino acid sequence as shown in SEQ ID NO:3) In a further embodiment, the VSSC confers resistance to an insecticide in *Musca domestica*, such as the VSSC encoded by the nucleotide sequence as shown in SEQ ID NO:3 (which encodes an amino acid sequence as shown in SEQ ID NO:4) Preferably, the insecticide resistant VSSC is encoded by a nucleic acid molecule having the nucleotide sequence of a second nucleic acid molecule with one or more mutations therein, wherein the second nucleic acid molecule encodes an insecticide sensitive VSSC, and wherein the one or more mutations in the second nucleic acid molecule render the resulting voltage-sensitive sodium channel resistant to an insecticide. For example, the nucleotide sequence of the second nucleic acid molecule may encode amino acid SEQ ID NO:3, and the insecticide resistant VSSC may have that amino acid sequence with one or more differences therein as follows: a substitution of phenylalanine for leucine at amino acid residue 1014 of SEQ ID NO:3; a substitution of isoleucine for methionine at amino acid residue 1140 of SEQ ID NO:3; a substitution of aspartic acid for glycine at amino acid residue 2023 of SEQ ID NO:3; a deletion of amino acid residues 2031–2034 of SEQ ID NO:3 (glycine-alanine-threonine-alanine); a substitution of threonine for serine at amino acid residue 2042 of SEQ ID NO:3; a substitution of alanine for valine at amino acid residue 2054 of SEQ ID NO:3; and an insertion of three amino acid residues (asparagine-glycine-glycine) after amino acid residue 2055 of SEQ ID NO:3 (between amino acid residues 2055 and 2056 of SEQ ID NO:3).

A variety of methodologies known in the art can be utilized to obtain an isolated VSSC according to the subject invention. In one method, the channel protein is purified from tissues or cells which naturally produce the channel protein. One skilled in the art can readily follow known methods for isolating proteins in order to obtain a member of the VSSC protein family, free of natural contaminants. These include, but are not limited to, immunochromatography, HPLC, size-exclusion chromatography, ion-exchange chromatography, and immunoaffinity chromatography. In another embodiment, a member of the VSSC family can be purified from cells which have been altered to express the channel protein. As used herein, a cell is said to be "altered to express the channel protein" when the cell, through genetic manipulation, is made to produce the channel protein which it normally does not produce or which the cell normally produces at low levels. One skilled in the art can readily adapt procedures for introducing and expressing either genomic, cDNA or synthetic sequences into either eukaryotic or prokaryotic cells in order to generate a cell which produces a member of the VSSC family utilizing the sequences disclosed herein.

A VSSC as defined herein includes molecules encoding VSSCs encoded by an amino acid sequence having at least 95% amino acid identity to SEQ ID NO:3 or to SEQ ID NO:4.

Antibodies can be raised to the voltage-sensitive sodium channel. Antibodies of the subject invention include polyclonal antibodies and monoclonal antibodies capable of binding to the channel protein, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the Fab2, and the Fd fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic channel protein (or an antigenic fragment thereof). Methods for immunization are well known in the art. Such methods include subcutaneous or intraperitoneal injection of the protein. One skilled in the art will recognize that the amount of the channel protein used for immunization will vary based on the animal which is immunized, the antigenicity of the protein, and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, etc. Procedures for accomplishing such labeling are well known in the art, for example see Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express a VSSC, to identify samples containing the VSSC proteins, or to detect the presence of a VSSC in a sample. More particularly, the antibodies or fragments thereof can thus be used to detect the presence of a VSSC in a sample, by contacting the sample with the antibody or fragment thereof. The antibody or fragment thereof binds to any VSSC present in the sample, forming a complex therewith. The complex can then be detected, thereby detecting the presence of the VSSC in the sample.

Fragments of the nucleic acid molecules encoding a VSSC are also provided, and are best defined in the context of amino acid sequence relationships among members of the VSSC sequence family and information on the function of specific VSSC domains. For example the amino acid sequence encoded by nucleotides 4648–4803 of SEQ ID NOs 1 or 2 encodes an amino acid sequence that is highly conserved among VSSC family members and is identified as the structural component forming the "inactivation gate" of sodium channels. Antibodies prepared to the polypeptide encoded by this fragment would therefore be expected to be of use as reagents capable of detecting many members of the VSSC family. Such antibodies, if introduced into cells that express VSSCs, would also be expected to modify the normal function of the VSSCs expressed in those cells. In contrast, the amino acid sequence encoded by nucleotides 3079–3852 of SEQ ID NOs 1 or 2 encodes an amino acid sequence that is less well conserved between the VSSCs of the insects *Musca domestica* and *Drosophila melanogaster*. Antibodies prepared to the polypeptide encoded by this fragment would therefore be expected to recognize selectively the VSSC from which the fragment was derived.

Also provided by the subject invention is a plasmid designated pPJI1 and deposited with the ATCC under Accession No. 97831, as well as a KpnI/AatII restriction fragment of about 3620 bp of the plasmid designated pPJI1. Further provided is a plasmid designated pPJI2 and deposited with the ATCC under Accession No. 97832, as well as an AatII/SphII restriction fragment of about 2700 bp of the plasmid designated pPJI2. When the above two restriction fragments are ligated together at their AatII sites, the resulting nucleic acid molecule encodes a voltage-sensitive sodium channel which confers susceptibility to an insecticide in *Musca domestica*. This resulting nucleic acid molecule is also provided by the subject invention.

MATERIALS AND METHODS

Heads of newly-emerged adult house flies (NAIDM or 538ge strain) (Knipple et al. 1994) were ground to a fine powder under liquid $N_2$ and extracted with acid guanidinium isothiocyanate/phenol/chloroform to obtain total RNA (Chomczynski and Sacchi 1987), which was fractionated on oligo(dT)-paramagnetic beads (PolyATtract mRNA isolation system; Promega, Madison, Wis.) to obtain poly(A$^+$) RNA. Pools of first strand cDNA were synthesized using either random hexamers (Harvey and Darlison 1991) or oligo(dT) adapted for the 3'-RACE procedure (Frohman and Martin 1989). These cDNA pools were employed as templates in the polymerase chain reaction (PCR) (Saiki et al. 1988) to amplify overlapping cDNA segments spanning the entire Vssc1 coding sequence. Mixed-sequence oligonucleotide primers employed for these amplifications comprised all possible sequence combinations encoding short (i.e., 6–8 residues) regions of amino acid conservation between the para gene of *D. melanogaster* and rat brain sodium channel I (Loughney et al. 1989; Knipple et al. 1991). In a few cases, mixed-sequence primers were based solely on the *D. melanogaster* sequence. Defined-sequence primers were derived either from the previously described 309-nucleotide exon of the house fly Vssc1 gene (Knipple et al. 1994) or from internal sequences of house fly cDNA fragments obtained by amplification with mixed-sequence primers. All primers were synthesized using an Applied Biosystems 392 instrument, deprotected using procedures provided by Applied Biosystems, desalted, and used without further purification. The sequences and designations of these primers are given in Table I. The methods and reagents employed in PCR amplifications are described elsewhere (Knipple et al. 1991; Henderson et al. 1994; Knipple et al. 1994); specific amplification conditions for each cDNA fragment were optimized by varying the annealing temperatures and extension times of the reaction. Following amplification, PCR products were separated from excess primers either by filtration of the reaction mixture through a Centricon-100 concentrator (Amicon, Beverly, Mass.) or by preparative electrophoresis on agarose gels, excision of the desired product, and extraction from the gel matrix (QIAquick spin column; Qiagen, Chatsworth, Calif.) prior to use as templates for DNA sequencing.

The DNA sequences of amplified cDNA fragments were determined by automated sequencing with an Applied Biosystems 373 instrument using fluorescently-labeled dideoxynucleotides and Taq DNA polymerase (PCR/Sequencing Kit; Applied Biosystems, Foster City, Calif.) in a modification of the dideoxynucleotide chain-termination method (Sanger et al. 1977). Sequencing of each amplification product was initiated by using the amplification primers to sequence inward from the termini, and additional primers were synthesized as needed to obtain the complete sequence of each strand. Mixed-sequence amplification primers were employed for sequencing at concentrations 10-fold higher than that used for defined-sequence primers. All sequence ambiguities and apparent polymorphisms were resolved by performing additional multiple sequencing reactions. The full-length Vssc1 coding sequences from the NAIDM and 538ge strains were compiled from 239 and 209 individual sequencing reactions, respectively, and were edited using the SeqEd software program (Applied Biosystems). Complete house fly Vssc1 sequences were analyzed and compared with published sodium channel sequences using the DNASTAR software package (DNASTAR, Madison, Wis.).

EXAMPLE I

Sequencing of the Insecticide Sensitive Vssc of House Fly

Figure 2:
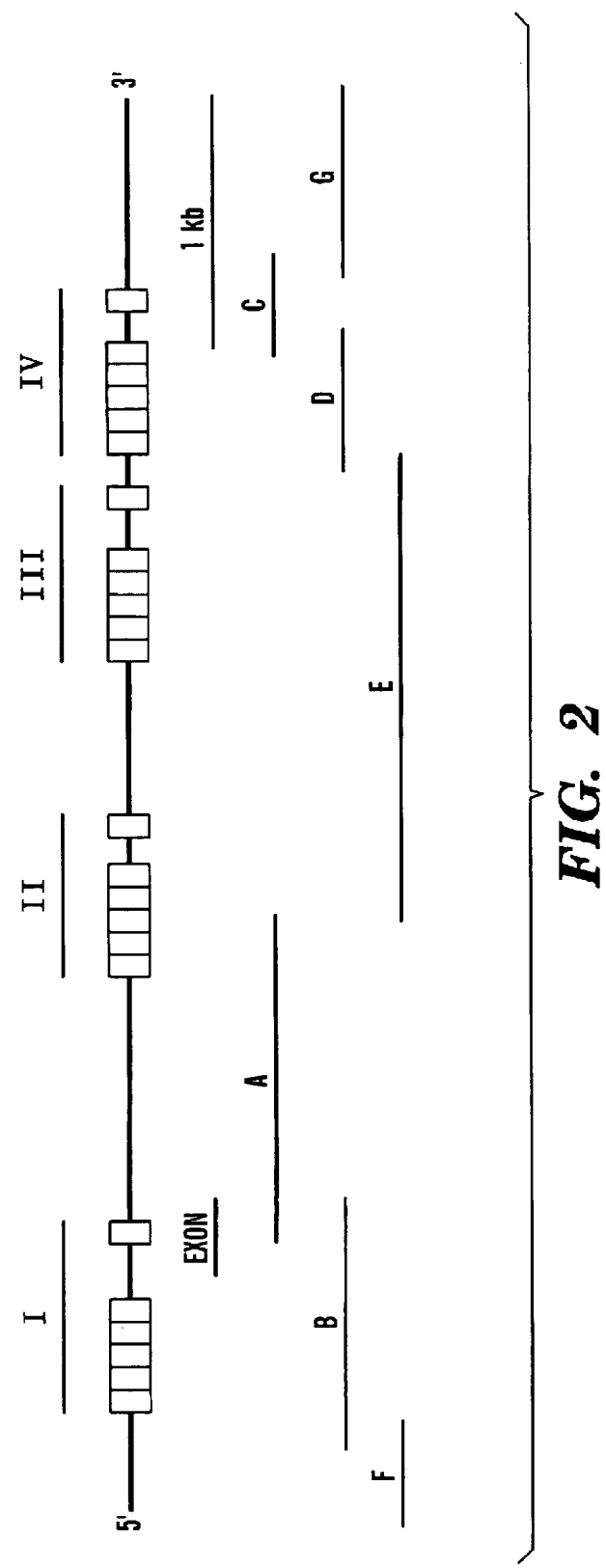
FIG. 2 is a diagram of the structural organization of the voltage-sensitive sodium channel coding sequence of *Musca domestica* (Vssc1) showing repeated homology domains I–IV and putative transmembrane helices (rectangles). Shown below the structural organization are the relative length and location of the previously-described 309-nucleotide exon of Vssc1 (Knipple et al. 1994) (exon) and seven overlapping PCR-amplified cDNA fragments (A–G) employed as templates for DNA sequencing.

As an expedient alternative to conventional iterative screenings of cDNA libraries, a sequencing strategy for the house fly Vssc1 gene was based on the PCR amplification and direct automated sequencing of overlapping cDNA fragments (FIG. 2). The point of entry for this strategy was the 309-nucleotide exon of the house fly Vssc1 gene identified previously from sequencing of cloned genomic DNA (Knipple et al. 1994). The use of defined-sequence primers from this region (Table I, A1 or B2) in combination with mixed-sequence primers encoding conserved amino acid sequences in either region IIS3 (A2) or the extracellular N-terminal domain (B1) gave cDNA fragments A and B. A second point of entry was established in homology domain IV using a pair of mixed-sequence primers (C1 and C2) to obtain fragment C. A primer (D2) designed from the internal sequence of fragment C, together with a mixed-sequence primer (D1) encoding a conserved amino acid motif in the short linker between homology domains III and IV, gave fragment D. A pair of defined-sequence primers (E1, E2) based on internal sequences of fragments A and D gave the large fragment E, which spanned most of homology domain II and all of homology domain III. Fragment F, corresponding to the 5' end of the coding sequence, was obtained using a defined-sequence primer (F2) derived from the internal sequence of fragment B and a mixed-sequence primer (F1) derived from a segment of the *D. melanogaster* sequence upstream from the translation start site (Loughney et al. 1989). Similarly, fragment G, containing the 3' end of the coding sequence, was obtained using a defined-sequence primer (G1) derived from the internal sequence of fragment C and a mixed-sequence primer (G2) derived from a segment of the *D. melanogaster* sequence downstream from the stop codon (Thackeray and Ganetzky 1994).

The complete coding sequence of the Vssc1$^{NAIDM}$ allele of the house fly, comprising a single open reading frame of 6318 nucleotides (SEQ ID NO:1), was determined by automated DNA sequencing using cDNA fragments A–G as templates (FIG. 2). This cDNA coded for a 2105-amino acid polypeptide (SEQ ID NO:3) with a predicted molecular weight of 236,671 Daltons that exhibited all of the common structural landmarks found in sodium channel a subunit genes (Catterall 1992; Kallen et al. 1993) (see FIG. 3) including four large internally homologous subdomains (I–IV), each containing six hydrophobic putative transmembrane helices (S1–S6) and a conserved sequence element between domains S5 and S6 identified as an ion pore-forming domain. The deduced Vssc1$^{NAIDM}$ amino acid sequence also contained a conserved element in the S4 region of each homology domain, characterized by a repeated motif of positively-charged amino acids that are thought to form the voltage-sensing element of the channel, and a short segment of conserved sequence between homology domains III and IV that has been identified as the channel inactivation gate (see FIG. 3). The deduced Vssc1$^{NAIDM}$ protein contained 10 potential sites for N-linked glycosylation (Kornfeld and Kornfeld 1985), 6 of which occur in putative extracellular regions. These regions of other sodium channel a subunit sequences are also known to contain potential glycosylation sites (Catterall 1992; Kallen et al. 1993).

Vertebrate sodium channels are known to undergo functional regulation as the result of phosphorylation by cAMP-dependent protein kinases at sites in the intracellular linker between homology domains I and II and by protein kinase C at a site in the intracellular linker between homology domains III and IV (Catterall 1992; Kallen et al. 1993). The deduced Vssc1$^{NAIDM}$ protein contained three potential cAMP-dependent protein kinase phosphorylation sites (Kemp and Pearson 1990) (Ser540, Ser557, and Ser628) in the cytoplasmic linker between homology domains I and II. The location of two of these (Ser540 and Ser557 of SEQ ID NO:3) corresponded to the cluster of four sites found in this region of vertebrate brain sodium channels that are implicated in sodium channel regulation (Catterall 1992). The deduced Vssc1$^{NAIDM}$ protein also contained three additional potential phosphorylation sites (Ser1167, Ser1207, and Ser2097 of SEQ ID NO:3) in other putative intracellular domains. The role of these phosphorylation sites in the regulation of insect sodium channels by cAMP-dependent protein kinase is not known. The deduced house fly voltage-sensitive sodium channel protein also contained two potential sites for protein kinase C phosphorylation (Ser1191 and Ser1582 of SEQ ID NO:3) (Kemp and Pearson 1990), the latter of which is the conserved site located within the inactivation gate sequence of the cytoplasmic linker between domains III and IV. Although the conservation of this site implicates a role for protein kinase C in the regulation of insect sodium channels, such an effect has not been demonstrated experimentally.

Figure 3B:
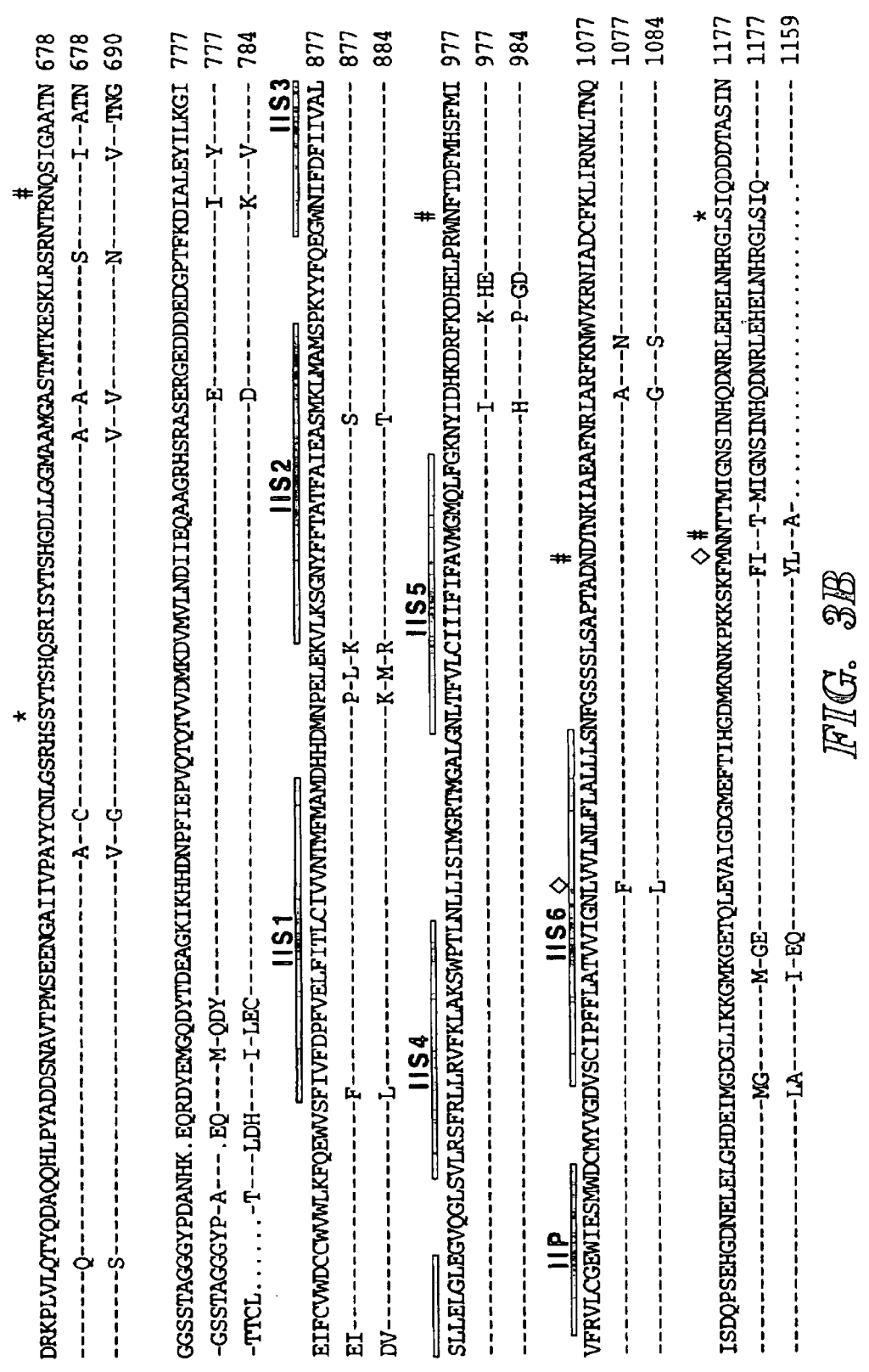

The deduced Vssc1$^{NAIDM}$ protein was 90.0% identical to the most similar variant of the para gene product of $D.$ $melanogaster$ (SEQ ID NO:19) (Loughney et al. 1989; Thackeray and Ganetzky 1994) (FIG. 3). The level of sequence identity was highest ($\geq$95%) in the N-terminal intracellular domain, the linker between homology domains III and IV, and homology domain IV. The level of sequence identity was lowest (73%) in the intracellular C-terminal domain. Alignment of the Vssc1 sequence with 12 other sodium channel α subunit sequences found in the GenBank database showed that the Vssc1 and para gene products exhibited approximately the same degree of sequence similarity as homologous sodium channel a subunit isoforms from different vertebrate species. These findings confirm and extend previous observations (Williamson et al. 1993; Knipple et al. 1994), based on fragmentary genomic DNA and cDNA sequences, of the high degree of sequence similarity between this house fly gene and the para gene of $D.$ $melanogaster$ and reinforce the conclusion that Vssc1 is the homolog of para in the house fly.

In $D.$ $melanogaster$ (Thackeray and Ganetzky 1994; O'Dowd et al. 1995) and $Drosophila$ $virilis$ (Thackeray and Ganetzky 1995), multiple sodium channel α subunit variants, each under specific developmental regulation, are generated from the para gene by the alternative usage of 8 exons (designated a–f, h, and i) located in homology domain II and portions of the cytoplasmic linker regions on either side of this domain. Given the heterogeneity of sodium channel-encoding sequences found in these Dipteran species, it was surprising to detect only a single sequence variant among the pool of amplified house fly head cDNA fragments. The Vssc1$^{NAIDM}$ sequence contained segments identical to exon a and homologous (21 identical amino acids out of 24) to exon i of $D.$ $melanogaster$. Recent studies suggest that both of these exons are required for the expression of high sodium current densities in embryonic $D.$ $melanogaster$ neurons (O'Dowd et al. 1995). In the region encoded by either exon c or exon d, the house fly sequence differs from both $D.$ $melanogaster$ sequences but is slightly more similar to exon d (50 identical amino acids out of 55) than to exon c (49 identical amino acids out of 55). The house fly sequence lacked segments homologous to $D.$ $melanogaster$ exons b, e, and f but contained a segment identical to exon h, which is a variable element found in some $D.$ $virilis$ sequences but not detected in $D.$ $melanogaster$. The house fly Vssc1$^{NAIDM}$ sequence described is thus characterized as structurally homologous to the a$^+$b$^-$c$^-$d$^+$e$^-$ f$^-$h$^+$i$^+$ splice variant of $D.$ $melanogaster$ and $D.$ $virilis$. The identification of this molecular form as the predominant sodium channel sequence variant in house fly heads was unexpected because it has not been detected among the arrays of splice variants detected in whole embryos or whole adults of either $D.$ $melanogaster$ or $D.$ $virilis$.

EXAMPLE II

Sequencing of the Insecticide Resistant Vssc of House Fly

Figure 4:
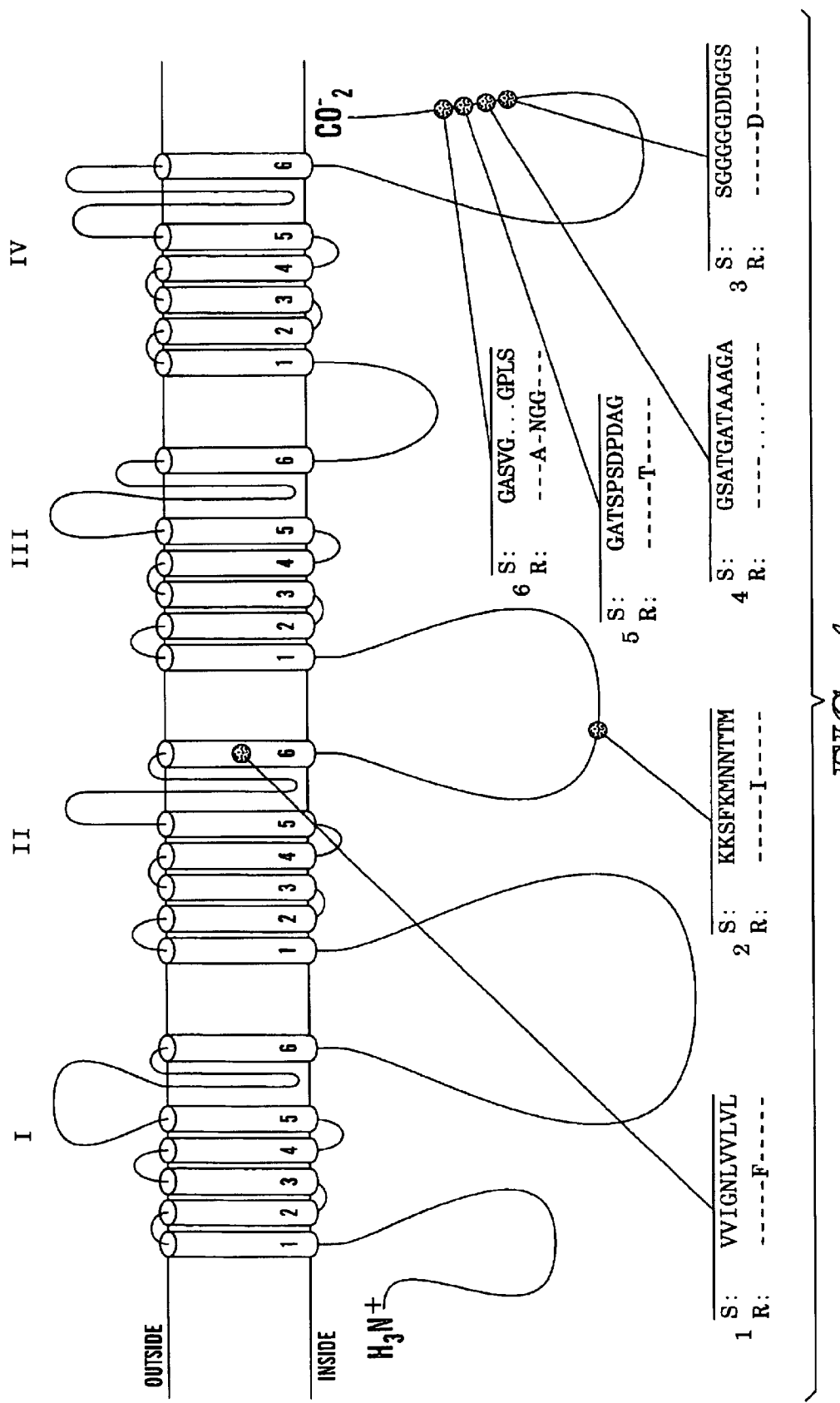
FIG. 4 is a diagram of the Vssc1 gene product showing the locations of 12 amino acid differences identified in the $Vssc1^{538ge}$ sequence, including 5 amino acid substitutions, 4 amino acid deletions, and 3 amino acid insertions in the $Vssc1^{538ge}$ sequence (R) as compared to the $Vssc1^{NAIDM}$ sequence (S)

The PCR amplification/sequencing strategy summarized in FIG. 2 was also employed to determine the sequence of Vssc1 cDNAs from heads of the 538ge house fly strain that carries the kdr trait. The nucleotide sequence of the VSSC of the 538ge house fly is shown in SEQ ID NO:2, and the amino acid sequence is shown in SEQ ID NO:4. The amino acid sequence of 2104 residues (SEQ ID NO:4) encoded by the Vssc1$^{538ge}$ cDNA contained 12 amino acid differences compared to that of the VSSc1$^{NAIDM}$ sequence (SEQ ID NO:3) as follows: a substitution of phenylalanine for leucine at amino acid residue 1014 of SEQ ID NO:3; a substitution of isoleucine for methionine at amino acid residue 1140 of SEQ ID NO:3; a substitution of aspartic acid for glycine at amino acid residue 2023 of SEQ ID NO:3; a deletion of amino acid residues 2031–2034 of SEQ ID NO:3 (glycine-alanine-threonine-alanine); a substitution of threonine for serine at amino acid residue 2042 of SEQ ID NO:3; a substitution of alanine for valine at amino acid residue 2054 of SEQ ID NO:3; and an insertion of three amino acid residues (asparagine-glycine-glycine) after amino acid residue 2055 of SEQ ID NO:3 (between amino acid residues 2055 and 2056 of SEQ ID NO:3). A comparison of the Vssc1$^{538ge}$ (SEQ ID NO:4) and Vssc1$^{NAIDM}$ (SEQ ID NO:3) amino acid sequences to the para sequence of the Canton-S strain of $D.$ $melanogaster$ (SEQ ID NO:19) is shown in FIG. 3. The locations and amino acid sequence context of the differences are shown in FIG. 4. In FIG. 4, S refers to the NAIDM amino acid sequence (SEQ ID NO:3), and R refers to the kdr sequence (SEQ ID NO:4) Dashes indicate that the Kdr sequence has the identical residue at that position as does the NAIDM sequence. The difference labeled 1 shows amino acids 1009–1019 of SEQ ID NO:3, with the amino acid substitution at residue 1014 shown. The difference labeled 2 shows amino acids 1135–1145 of SEQ ID NO:3, with the amino acid substitution at residue 1140 shown. The difference labeled 3 shows amino acids 2018–2028 of SEQ ID NO:3, with the amino acid substitution at residue 2023 shown. The difference labeled 4 shows amino acids 2027–2038 of SEQ ID NO:3, with the deletion of residues 2031–2034 shown. The difference labeled 5 shows amino acids 2037–2047 of SEQ ID NO:3, with the amino acid substitution at residue 2042 shown. The difference labeled 6 shows amino acids 2051–2059 of SEQ ID NO:3, with the amino acid substitution at residue 2054 shown and the insertion of three residues between 2055 and 2056 shown.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Names and sequences of oligonucleotide primers used in the PCR amplification of partial Vssc1 cDNAs.

| Name | Sequence | |
|------|----------|---|
| A1 | 5'-CGGTTGGGCTTTCCTGTC-3' | SEQ ID NO:5 |
| A2 | 5'-GGGAATTCRAADATRTTCCANCCYTC-3' | SEQ ID NO:6 |
| B1 | 5'-CCCGARGAYATHGAYCYNTAYTA-3' | SEQ ID NO:7 |
| B2 | 5'-CGTATCGCCTCCTCCTCG-3' | SEQ ID NO:8 |
| C1 | 5'-GGGTCTAGATHTTYGCNATHTTYGGNATG'3' | SEQ ID NO:9 |
| C2 | 5'-GGGGAATTCNGGRTCRAAYTGYTGCCA-3' | SEQ ID NO:10 |
| D1 | 5'-GGGTCTAGARGANCARAARAARTAYTA-3' | SEQ ID NO:11 |
| D2 | 5'-TCATACTTTGGCCCAATGTC-3' | SEQ ID NO:12 |
| E1 | 5'-CCCGAATTAGAGAAGGTGCTG-3' | SEQ ID NO:13 |
| E2 | 5'-ACTATTGCTTGTGGTCGCCAC-3' | SEQ ID NO:14 |
| F1 | 5'-CATCNTTRGCNGCNTAGACNATGAC-3' | SEQ ID NO:15 |
| F2 | 5'-GATTGAATGGATCGAGCAGCC-3' | SEQ ID NO:16 |
| G1 | 5'-CGTTTCTCCTTTCATATCTAG-3' | SEQ ID NO:17 |
| G2 | 5'-GGAGBGGBGGNCKBGGNCKNGCTCA-3' | SEQ ID NO:18 |

Designation of oligonucleotide mixtures:
B = G + T + C;
D = G + A + T;
H = A + T + C;
K = G + T;
N = A + C + G + T;
R = A + G;
Y = C + T.

LIST OF REFERENCES CITED

Barchi, R. L., Probing the Molecular Architecture of the Voltage-Dependent Sodium Channel in "The Molecular Biology of Receptors, Pumps, and Channels: Pharmacological Targets," ASPET Meeting Abstracts; (August 1988).

Bayer, E. A., et al., *Meth Enzym* 62:308 (1979).

Bloomquist, J. R. In Reviews in Pesticide Toxicology (Edited by M. Roe and R. J. Kuhr), pp. 181–226. Toxicology Communications, Raleigh, N.C. (1993).

Bloomquist, J. R., and Soderlund, D. M., *Mol Pharmacol* 33:543–550 (1988).

Bordo, D. and Argos, P., *J. Mol Biol* 217:721–729 (1991).

Campbell, A. M., "Monoclonal Antibody Technology: Laboratory Techniques in Biochemistry and Molecular Biology", Elsevier Science Publishers, Amsterdam, The Netherlands (1984).

Capecchi, M., *Cell* 22:479–488 (1980).

Catterall, W. A. et al., *Molec Pharmacol* 20:533–542 (1981).

Catterall, W. A., *Ann Rev Biochem* 55:953–985 (1986).

Catterall, W. A., *Physiological Reviews* 72(4):S14–S48 (1992).

Chomczynski, P. and Sacchi, N., *Anal Biochem* 162:156–159 (1987).

Chrisey, L., et al., *Antisense Research and Development* 1(1):57–63 (1991).

Christoffersen, R. E. and Marr, J. J., *Journal of Medicinal Chemistry* 38(12):2023–2037 (1995).

Deri, Z. and Adam-Vizi, V., *J Neurochem* 61:818–825 (1993).

Eldefrawi et al., *FASEB J* 1:262–271 (1987).

Engval, E. et al., *Immunol* 109:129 (1972).

Feng, G., et al., *Cell* 82:1001–1011 (1995).

Frelin, C., et al., *Pflugers Arch* 402:121–128 (1984).

French, S. and Robson, B., *J Molecular Evolution* 19:171–175 (1983).

Frohman, M. A. and Martin, G. R., *Technique* 1:165–170 (1989).

Goding, J. W., *J Immunol Meth* 13:215 (1976).

Han, L., et al., *Proc Natl Acad Sci USA* 88:4313–4317 (1991).

Harvey, R. J. and Darlison, M. G., *Nucl Acids Res* 19:4002 (1991).

Henderson, J. E., et al., *Insect Biochem. Mol Biol* 24:363–371 (1994).

Innis, et al., *PCR Protocols*, Academic Press, San Diego, Calif. (1990).

Isom, et al., *Science* 256:839–842 (1992).

Isom, et al., *Neuron* 12:1183–1194 (1994).

Jacques, Y., et al., *J Biol Chem* 253(20):7383–7392 (1978).

Johansen, H., et al., *Genes & Development* 3:882–889 (1989).

Kallen, R. G., et al., *Mol Neurobiol* 7:383–428 (1993).

Kemp, B. E. and Pearson, R. B., *Trends Biochem Sci* 15:342–346 (1990).

Klein, T. M., et al., *Nature* 327:70–73 (1987).

Knipple, D. C., et al., *Proc Natl Acad Sci USA* 91:2483–2487 (1994).

Knipple, D. C., et al., *Arch Insect Biochem Physiol* 16:45–53 (1991).

Kornfeld, R. and Kornfeld, S., *Annu Rev Biochem* 54:931–664 (1985).

Loughney, K., et al., *Cell* 58:1143–1154 (1989).

Lutz, et al., *Exp Cell Res* 175:109–124 (1988).

Mannino, R. J. and Gould-Fogerite, S., *BioTechniques* 6:682–690 (1988).

Miller, L. K., *Bioessays* 11:91–95 (1989).

Moczydlowski, E., et al., *Proc Natl Acad Sci USA* 83:5321–5325 (1986).

Noda, M., et al., *Nature* 312:121–127 (1984).

Noda, M., et al., *Nature* 320:188–192 (1986).

O'Dowd, D. K., et al., *J Neurosci* 15:4005–4012 (1995).

Okamoto et al., *Proc Jpn Acad* 63:284–288 (1987).

Ramaswami and Tanouye, *Proc Natl Acad Sci USA* 86:2079–2082 (1989).

Rauh et al., *Trends in Pharmacol Sci* 11:325–329 (1990).

Rogart, R. B., *Ann New York Acad Sci* 479:402–430 (1986).

Rossi, J. J., *British Medical Bulletin* 51(1):217–225 (1995).

Rossi, J. J., et al., *AIDS Research and Human Retroviruses* 8(2):183–189 (1992).

Saiki, R. K., et al., *Science* 239:487–491 (1988).

Sambrook et al. Molecular Cloning: A Laboratory Manual, 2d Edition, Cold Spring Harbor Laboratory Press, Cold Spring Harbor, N.Y. (1989).

Sang, J. H., *Adv Cell Culture* 1:125–182 (1981).
Sanger, F., et al., *Proc Natl Acad Sci USA* 74:5463–5467 (1977).
Sarver, N., et al., *Science* 247:1222–1225 (1990).
Sawicki, R. M., *Nature* 275(5679):443–444 (1978).
Shigekawa, K. and Dower, W. J., *BioTechniques* 6:742–751 (1988).
Smith, G. E., et al., *Mol Cell Biol* 3:2156–2165 (1983).
Soderlund, D. M. and Bloomquist, J. R. *Annu Rev Entomol* 34:77–96 (1989).
Soderlund, D. M. and Bloomquist, J. R., in *Pesticide Resistance in Arthropods* (Edited by R. T. Roush and B. E. Tabashnik), pp. 58–96. Chapman and Hall, New York, N.Y. (1990).
Soderlund, D. M., and Knipple, D. C., in *Molecular Action of Insecticides on Ion Channels*, eds. Clark, J. M., American Chemical Society, Washington, D.C., pp. 97–108 (1994).
St. Groth, et al., *J Immunol Methods* 35:1–21 (1980).
Sternberger, L. A., et al., *J Histochem Cytochem* 18:315 (1970).
Stuhmer, W., *Methods in Enzymology* 207:319–339 (1992).
Suzuki et al., *Proc Natl Acad Sci USA* 68:890–893 (1971).
Taglialatela, M., et al., *Biophys J* 61:78–82 (1992).
Taylor, W. R., *J Theor Biol* 119:205–218 (1986).
Thackeray, J. R. and Ganetzky, B., *J Neurosci* 14:2569–2578 (1994).
Thackeray, J. R. and Ganetzky, B., *Genetics* 141:203–214 (1995).
Williamson, M. S., et al., *Mol Gen Genet* 240:17–22 (1993).

What is claimed is:

1. A method of screening a chemical agent for the ability of the chemical agent to modify sodium channel function, said method comprising:

introducing an isolated nucleic acid molecule encoding a voltage-sensitive sodium channel of *Musca domestica*, wherein said nucleic acid molecule hybridizes to a nucleic acid molecule having a nucleotide sequence according to SEQ. ID. NOS: 1 or 2 at 42° C., with 5×SSPC and 50 percent formamide with washing at 65° C. with 0.5×SSPC into a eukaryotic host cell in vitro;

expressing said voltage-sensitive sodium channel encoded said nucleic acid molecule in the host cell so as to result in the functional expression of said voltage-sensitive sodium channel in the host cell;

exposing the host cell to a chemical agent; and evaluating the exposed host cell to determine if the chemical agent modifies sodium channel function.

2. The method of claim 1 wherein the host cell is a *Xenopus oocyte*.

3. The method of claim 1 wherein the host cell is an insect cell line.

4. The method of claim 3 wherein said insect cell line is selected from the group consisting of a *Drosophila Schneider* cell line, a Drosophila $K_c$ cell line, an Sf9 cell line, and a High Five® cell line.

5. The method of claim 1 wherein the evaluation comprises monitoring sodium transport through said voltage-sensitive sodium channel.

6. The method of claim 1 wherein the evaluation comprises monitoring quanidinium transport through said voltage-sensitive sodium channel.

7. The method according to claim 1, wherein said voltage-sensitive sodium channel confers susceptibility to an insecticide in *Musca domestica*.

8. The method according to claim 7, wherein said nucleotide sequence as shown in SEQ ID NO:1.

9. The method of claim 7, wherein said nucleic acid molecule encodes an amino acid sequence as shown in SEQ ID NO:3.

10. The method according to claim 1, wherein said voltage-sensitive sodium channel confers resistance to an insecticide in *Musca domestica*.

11. The method according to claim 10, wherein said voltage-sensitive sodium channel is encoded by the nucleotide sequence as shown in SEQ ID NO:2.

12. The method according to claim 1, wherein said nucleic acid molecule encodes an amino acid sequence as shown in SEQ ID NO:4.

13. A method of screening a chemical agent for the ability of the chemical agent to modify sodium channel function, said method comprising:

introducing a first nucleic acid molecule encoding a voltage-sensitive sodium channel of *Musca domestica* and a second nucleic acid molecule encoding a tip E protein into a eukaryotic host cell in vitro, wherein said first nucleic acid molecule hybridizes to a nucleic acid molecule having a nucleotide sequence according to SEQ ID NOS: 1 or 2 at 42° C., with 5×SSPC and 50 percent formamide with washing at 65° C. with 0.5× SSPC;

allowing said host cell to coexpress said first nucleic acid molecule and said second nucleic acid molecule so as to result in the functional expression of said voltage-sensitive sodium channel in the host cell;

exposing the host cell to a chemical agent; and evaluating the exposed host cell to determine if the chemical agent modifies sodium channel function.

14. The method of claim 13 wherein the host cell is a *Xenopus oocyte*.

15. The method of claim 13 wherein the host cell is an insect cell line.

16. The method of claim 15 wherein said insect cell line is selected from the group consisting of a *Drosophila Schneider* cell line, a Drosophila $K_c$ cell line, an Sf9 cell line, and a High Five® cell line.

17. The method of claim 13 wherein the evaluation comprises monitoring sodium transport through said voltage-sensitive sodium channel.

18. The method of claim 13 wherein the evaluation comprises monitoring quanidinium transport through said voltage-sensitive sodium channel.

* * * * *

SEQUENCE LISTING

<160> NUMBER OF SEQ ID NOS: 19

<210> SEQ ID NO 1
<211> LENGTH: 6318
<212> TYPE: DNA
<213> ORGANISM: Musca domestica

<400> SEQUENCE: 1

```
atgacagaag attccgactc gatatctgag gaagaacgca gtttgttccg tcccttcacc      60
cgcgaatcat tgttacaaat cgaacaacgt atcgctgaac atgaaaaaca aaaggagctg     120
gaaagaaaga gagccgccga aggagagcag atacgatatg atgacgagga cgaagatgaa     180
ggtccacagc cggatcccac acttgaacag ggtgtgccta tacctgttcg aatgcagggc     240
agcttcccgc cggaattggc ctccactcct ctcgaggata tcgatccctt ctacagtaat     300
gtactgacat ttgtagtaat aagtaaagga aaggatattt ttcgtttttc tgcctcaaaa     360
gcaatgtggc tgctcgatcc attcaatccg atacgtcgtg tagccattta tattttagtg     420
catcccttgt tttcgttatt cattatcacc actattctaa ctaattgtat tttaatgata     480
atgccgacaa cgcccacggt cgaatccaca gaggtgtatat tcaccggaat ctacacattt     540
gaatcagctg ttaaagtgat ggcacgaggt ttcatttat gcccgtttac gtatcttaga      600
gatgcatgga attggctgga cttcgtagta atagctttag cttatgtgac catgggcata     660
gatttaggta atctcgcagc tttgagaaca tttagggtac tgcgagctct gaaaaccgta     720
gccattgtgc caggtctaaa aaccattgtc ggtgctgtca ttgaatctgt aaaaaatcta     780
cgcgatgtga taattttgac aatgttttcc ctgtcggtgt tcgcgctgat gggcctacaa     840
atctatatgg tgttctaac acaaaagtgc attaaacgat tccccctgga cggcagttgg     900
ggcaatctga ccgatgaaaa ctggtttcta cacaatagca acagttccaa ttggtttacg     960
gagaacgatg gcgagtcata tccggtgtgc gggaatgtat ccggtgcggg acaatgcggc    1020
gaggattacg tctgcctgca gggcttcggc cccaatccca actacgacta caccagtttc    1080
gattcattcg gttgggcttt cctgtcggcg tttcgtctca tgacccaaga tttctgggag    1140
gatctgtatc agcacgtgct gcaagcagct ggaccctggc acatgttgtt ctttatagtc    1200
atcatcttcc taggttcatt ctatcttgtg aatttgattt tggccattgt tgccatgtct    1260
```

-continued

```
tatgacgaat tgcaaaagaa ggccgaagaa gaagaggctg ccgaggagga ggcgatacga      1320
gaagctgaag aagcggcagc agccaaggcg gccaaactgg aggagcgggc caatgtagca      1380
gctcaagcgg ctcaggatgc agcggatgcc gctgcggcag ctctgcatcc cgagatggca      1440
aagagtccca cgtactcttg cattagctat gaactgtttg ttggcggcga aagggcaac      1500 gatgacaaca acaaagagaa gatgtccata cgcagcgtcg aagtggaatc ggagtcggtg      1560
agcgttatac aaagacaacc agcacctacc acagcacccg ctactaaagt ccgtaaagtt      1620
agcacgactt ccttatcctt acctggttca ccatttaacc tacgccgggg atcacgtagt      1680
tcacacaagt acacaatacg aaatgggcgt ggacgttttg gtataccagg tagcgatcgc      1740
aagccattgg tactgcaaac atatcaggat gcccagcagc atttgcccta tgccgatgac      1800
tcgaatgccg taacaccaat gtccgaagag aatggtgcca ttatagtacc agcctactat      1860
tgtaatttag gttctagaca ttcttcatat acctcgcatc aatcaagaat ctcgtataca      1920
tcacatggtg atttattggg tggcatggcg ccatggggtg ccagcacaat gaccaaagag      1980
agcaaattgc gcagtcgcaa cacacgcaat caatcaatcg gtgctgcaac caatggtggc      2040
agtagtacgc tggtggtgg ctatcccgat gccaatcaca aggaacaaag ggattatgaa       2100
atgggtcagg attatacaga cgaagctggc aaaataaaac accacgacaa tccttttatc      2160
gagcccgtcc aaactcaaac agtggtagac atgaaagatg ttatggtctt aaatgatatc      2220
attgaacaag ccgctggtcg gcatagtcgt gctagtgaac gaggtgagga cgatgacgaa      2280
gatggtccca cattcaagga catcgccctc gaatacatcc taaaaggcat cgaaatcttt      2340
tgtgtatggg actgttgttg ggtgtggtta aaatttcagg aatgggtgtc ctttattgtg      2400
ttcgatccat tcgtggagct cttcattacc ctgtgtattg tggtcaatac gatgtttatg      2460
gccatggatc atcacgacat gaatccggaa ttagagaagg tgctgaaaag tggtaactat      2520
ttcttcacgg ccacttttgc aattgaagcc agcatgaaac tgatggccat gagcccgaag      2580
tactacttcc aggaaggctg gaacattttc gatttcatta ttgtggcctt gtctctgctg      2640
gaattgggcc tggaggtgt ccagggcctg tcggtgttga aagttttcg tttgcttcgt        2700 gtattcaaat tggcaaaatc atggcccaca ctcaatttac tcatttcgat tatgggccgg      2760
acaatgggtg cattgggtaa tctgacattt gtactttgca ttatcatctt catctttgcc      2820
gtgatgggaa tgcaacttt cggaaagaac tatattgacc acaaggatcg cttcaaggac       2880
catgaattac cgcgctggaa cttcaccgac ttcatgcaca gcttcatgat tgtgttccga      2940
gtgctgtgcg gagagtggat cgagtccatg tgggactgca tgtatgtggg cgatgtcagc     3000 tgtatacccct tcttcttggc cacggtcgtg ataggcaatc ttgtggttct taatcttttc     3060
ttagctttgc ttttgtccaa cttcggttca tctagtttat cagccccgac tgccgacaat     3120
gataccaata aaatagcaga ggccttcaat cgtattgctc gttttaagaa ctgggtgaaa     3180
cgtaatattg ccgattgttt taagttaatt cgaaatataat tgacaaatca ataagtgac    3240 caaccatcag aacatggcga taatgaactg gagttgggtc atgacgaaat catgggcgat     3300
ggcttgatca aaaagggtat gaagggcgag acccagctgg aggtggccat ggcgatggc     3360 atggagttca cgatacatgg cgatatgaaa acaacaagc cgaagaaatc aaaattcatg      3420
aacaacacaa cgatgattgg aaactcaata accaccaag acaatagact ggaacatgag       3480
ctaaaccata gaggtttgtc catacaggac gatgacactg ccagcattaa ctcatatggt      3540
agccataaga atcgaccatt caaggacgag agccacaagg gcagcgccga gaccatcgag      3600
ggcgaggaga aacgcgacgt cagcaaagag gacctcggcc tcgacgagga actggacgag      3660
```

```
gaggccgagg gcgatgaggg ccagctggat ggtgacatta tcattcatgc gcaaaacgac    3720
gacgagataa tcgacgacta tccggccgac tgtttccccg actcgtacta caagaagttt    3780
ccgatcttgg ccggcgacga ggactcgccg ttctggcaag gatggggcaa tttacgactg    3840
aaaactttc aattaattga aataaatat tttgaaaccg cagttatcac tatgatttta     3900
atgagtagct tagctttggc cttagaagat gttcatttac ccgatcgacc tgtcatgcag    3960
gatatactgt actacatgga caggatattt acggtgatat tcttttgga gatgttgatc     4020
aaatggttgg ccctgggctt taaggtttac ttcaccaatg cctggtgttg gctggatttc    4080
gtgattgtca tgctatcgct tataaatttg gttgccgttt ggtcgggctt aaatgatata    4140
gccgtgttta gatcaatgcg cacactgcgc gccctaaggc cattgcgtgc tgtctctaga    4200
tgggagggta tgaaagttgt cgtgaatgcg ctggttcaag ctataccgtc catcttcaat    4260
gtgctattgg tgtgtctgat attttggctt attttttgcca ttatgggagt acagcttttt   4320
gctggaaaat attttaagtg taaagatggt aatgacactg tgctgagcca tgaaatcata    4380
ccgaatcgta atgcctgcaa aagtgaaaac tacacctggg aaaattcggc aatgaacttc    4440
gatcatgtag gtaatgcgta tctctgtcta tttcaagtgg ccacctttaa gggctggatc    4500
cagattatga acgatgccat tgattcacga gaggtggaca agcagccgat ccgagaaacc    4560
aatatctaca tgtatttata tttcgtattc ttcattatat ttggatcatt tttcacactc    4620
aatctgttca ttggtgttat cattgataat tttaatgaac aaaagaagaa agctggtgga    4680
tcattagaaa tgttcatgac agaagatcag aaaaagtact ataatgctat gaaaaagatg    4740
ggctctaaaa aaccattaaa agccattcca agaccgaggt ggcgaccaca agcaatagta    4800
ttcgaaatag ttacagataa aaaattcgat ataatcatta tgttgttcat ggcttaaac    4860
atgtttacca tgaccctcga tcggtacgac gcctccgagg cgtacaacaa tgtcctcgac    4920
aaactcaatg ggatattcgt agttatttc agtggcgaat gtctattaaa aatattcgct    4980
ttacgatatc actatttcaa agagccatgg aatttatttg atgtagtagt tgtcattta    5040
tccatcttag gtcttgtact cagcgacatc attgagaagt atttcgtatc gccgacactg    5100
ctccgtgtgg tgagagtggc caaagtgggt cgtgtcctgc gtttagtcaa gggtgccaag    5160
ggtatccgga cgttgctgtt cgcgttagcc atgtcgttgc ctgccttatt caacatttgt    5220
ctgttgctgt tcttggtgat gttcatcttt gctatctttg gcatgtcctt cttcatgcat    5280
gtcaaagaga agagcggcat aaatgctgtg tataatttta agacatttgg ccaaagtatg    5340
atattgctgt tcagatgtc tacctcagcc ggttgggatg gtgtgttaga tgccattatc    5400
aatgaggaag attgcgatcc acccgacaac gacaagggct atccgggcaa ttgtggttca    5460
gcgactgttg gaattacgtt tctcctttca tatctagtta taagctttt gatagttatt    5520
aatatgtaca ttgctgtcat tctcgagaac tatagccagg ctacgaggga tgtacaggag    5580
ggtctcaccg acgacgatta cgatatgtac tacgagattt ggcaacaatt cgatccggag    5640
ggcacccagt acatacgcta cgaccagctg tccgagtttc tggacgtgct ggagccgccg    5700
ctgcagatcc acaagccgaa caagtacaaa atcatatcga tggacatgcc gatatgtcgg    5760
ggcgacatga tgtactgtgt ggatatattg gatgccctga ccaaggactt ctttgcgcgc    5820
aagggtaatc cgatcgagga gacgggtgaa attggtgaga tagcggcgcg accggacacc    5880
gagggctatg atccggtgtc gtcaacactg tggcgccagc gtgaggagta ctgcgccaag    5940
ctgatacaga atgcgtggcg gcgttacaag aatggcccac cccaggaggg tgatgagggc    6000
```

```
gaggcggctg gtggcgaaga tggtgctgaa ggcggtgagg gtgaaggagg cagcggcggc      6060
ggcggcggtg atgatggtgg ctcagcgaca ggagcaacgg cggcggcggg agccacatca      6120
ccctcagatc cagatgccgg cgaagcgagt ggtgccagcg tcggcggccc ccttagtccg      6180
ggctgtgtta gtggcggcag taatggccgc caaacggccg tactggtcga aagcgatggt      6240
tttgttacaa aaaacggtca taaggttgta atacactcga gatcgccgag cataacatcc      6300
aggacggcag atgtctga                                                    6318

<210> SEQ ID NO 2
<211> LENGTH: 6315
<212> TYPE: DNA
<213> ORGANISM: Musca domestica

<400> SEQUENCE: 2
atgacagaag attccgactc gatatctgag gaagaacgca gtttgttccg tcccttcacc       60
cgcgaatcat tgttacaaat cgaacaacgt atcgctgaac atgaaaaaca aaaggagctg      120
gaaagaaaga gagccgccga aggagagcag atacgatatg atgacgagga cgaagatgaa      180
ggtccacagc cggatcccac acttgaacag ggtgtgccta tacctgttcg aatgcagggc      240
agcttcccgc cggaattggc ctccactcct ctcgaggata tcgatccctt ctacagtaat      300
gtactgacat ttgtagtaat aagtaaagga aaggatattt tcgttttttc tgcctcaaaa      360
gcaatgtggc tgctcgatcc attcaatccg atacgtcgtg tagccattta tattttagtg      420
catcccttgt tttcgttatt cattatcacc actattctaa ctaattgtat tttaatgata      480
atgccgacaa cgcccacggt cgaatccaca gaggtgatat tcaccggaat ctacacattt      540
gaatcagctg ttaaagtgat ggcacgaggt ttcattttat gcccgtttac gtatcttaga      600
gatgcatgga attggctgga cttcgtagta atagctttag cttatgtgac catgggcata      660
gatttaggta atctcgcagc tttgagaaca tttagggtac tgcgagctct gaaaaccgta      720
gccattgtgc aggtctaaa aaccattgtc ggtgctgtca ttgaatctgt aaaaaatcta      780
cgcgatgtga taattttgac aatgttttcc ctgtcggtgt tcgcgctgat gggcctacaa      840
atctatatgg gtgttctaac acaaaagtgc attaaacgat tcccctggaa cggcagttgg      900
ggcaatctga ccgatgaaaa ctggtttcta cacaatagca acagttccaa ttggtttacg      960
gagaacgatg gcgagtcata tccggtgtgc gggaatgtat ccggtgcggg acaatgcggc     1020
gaagattacg tctgcctgca gggcttcggc cccaatccca actacgacta caccagtttc     1080
gactcattcg gttgggcttt cctgtcggcg tttcgtctca tgacccaaga tttctgggag     1140
gatctgtatc agcacgtgct gcaagcagct ggaccctggc acatgttgtt ctttatagtc     1200
atcatcttcc taggttcatt ctatcttgtg aatttgattt tggccattgt tgccatgtct     1260
tatgacgaat tgcaaaagaa ggccgaagaa gaagaggctg ccgaggagga ggcgatccga     1320
gaagctgaag aagcggcagc agccaaggcg gccaaactgg aggagcgggc caatgtagca     1380
gctcaagcgg ctcaggatgc agcggatgcc gctgcggcag ctctgcatcc gagatggca     1440 aagagtccca cgtactcttg cattagctat gaactgtttg ttggcggcga aagggcaac     1500 gatgacaaca caaggagaa gatgtcgata cgcagcgtcg aagtggaatc ggagtcggtg     1560
agcgttatac aaagacaacc agcacctacc acagcacccg ctactaaagt ccgtaaagtt     1620
agcacgactt ccttatcctt acctggttca ccatttaacc tacgccgggg atcacgtagt     1680
tcacacaagt acacaatacg aaatgggcgt ggacgttttg gtataccagg tagcgatcgc     1740
aagccattgg tactgcaaac atatcaggat gcccagcagc atttgcccta tgccgatgac     1800
```

-continued

```
tcgaatgccg taacaccaat gtccgaagag aatggtgcca ttatagtacc agcctactat    1860
tgtaatttag gttctagaca ttcttcatat acctcgcatc aatcaagaat ctcgtataca    1920
tcacatggtg atttattggg tggcatggcg gccatgggtg ccagcacaat gaccaaagag    1980
agcaaattgc gcagtcgcaa cacacgcaat caatcaatcg gtgctgcaac caatggtggc    2040
agtagtacgc ccggtggtgg ctatcccgat gccaatcaca aggaacaaag ggattatgaa    2100
atgggtcagg attatacaga cgaagctggc aaaataaaac accacgacaa tcctttatc     2160 gagcccgtcc aaactcaaac agtggtagac atgaaagatg ttatggtctt aaatgatatc    2220
attgaacaag ccgctggtcg gcatagtcgt gctagtgaac gaggtgagga cgatgacgaa    2280
gatggtccca cattcaagga catcgccctc gaatatatcc taaaaggcat cgaaatcttt    2340
tgtgtatggg actgttgttg ggtgtggtta aaatttcagg aatgggtctc ctttattgtg    2400
ttcgatccat tcgtggagct cttcattacc ctgtgtattg tggtcaatac aatgttcatg    2460
gccatggatc atcacgacat gaatccggaa ttggagaagg tgctgaaaag tggtaactat    2520
ttcttcacgg ccacttttgc aattgaggcc agcatgaaac tgatggccat gagcccgaag    2580
tactacttcc aggaaggctg gaacattttc gatttcatta ttgtggcctt gtctctgctg    2640
gaattgggcc tggagggtgt ccagggcctg tcggtgttga agtttttcg tttgcttcgt     2700 gtattcaaat tggcaaaatc atggcccaca ctgaatttac tcatttcgat tatgggccgg    2760
acaatgggtg cattgggtaa tctgacattt gtactttgca ttatcatctt catctttgcc    2820
gtgatgggaa tgcaactttt cggaaagaac tatattgacc acaaggatcg cttcaaggac    2880
catgaattac cgcgctggaa tttcaccgac ttcatgcaca gcttcatgat tgtgttccga    2940
gtgctgtgcg gagagtggat cgagtccatg tgggactgca tgtatgtggg cgatgtcagc    3000
tgtataccct tcttcttggc cacggtcgtg atcggcaatt tgtggttct taatctttc      3060 ttagctttgc ttttgtccaa cttcggttca tctagtttat cagccccgac tgccgacaat    3120
gataccaata aaatagcaga ggccttcaat cgtattgctc gttttaagaa ctgggtgaaa    3180
cgtaatattg ccgattgttt taagttaatt cgaaataaat tgacaaatca ataagtgac    3240 caaccatcag aacatggcga taatgaactg gagttgggtc atgacgaaat catgggcgat    3300
ggcttgatca aaagggtat gaaggggcgag acccagctgg aggtggccat ggcgatggc     3360 atggagttca cgatacatgg cgatatgaaa acaacaagc ccaagaaatc aaaattcata     3420
aacaacacaa cgatgattgg aaactcaata accaccaag acaatagact ggaacatgag     3480
ctaaaccata gaggtttgtc catacaggac gatgacactg ccagcattaa ctcatatggt    3540
agccataaga atcgaccatt caaggacgag agccacaagg gcagcgccga gaccatcgag    3600
ggcgaggaga aacgcgacgt cagcaaagag gacctcggcc tcgacgagga actggacgag    3660
gaggccgagg gcgatgaggg ccagctggat ggtgacatca tcattcatgc ccaaaacgac    3720
gacgagataa tcgacgacta tccggccgac tgtttccccg actcgtacta caagaagttt    3780
ccgatcttgg ccggcgacga ggactcgccg ttctggcaag gatggggcaa tttacgactg    3840 aaaactttc aattaattga aaataaatat tttgaaaccg cagttatcac tatgatttta     3900
atgagtagct tagctttggc cttagaagat gttcatttac ccgatcgacc tgtcatgcag    3960
gatatactgt actacatgga caggatattt acggtgatat tctttttgga gatgttgatc    4020 aaatggtttgg ccctgggctt taaggtctac ttcaccaatg cctggtgttg gctggatttc    4080
gtgattgtca tgctatcgct tataaatttg gttgccgttt ggtcgggctt aaatgatata    4140
```

```
gccgtgttta gatcaatgcg cacactgcgc gccctaaggc cattgcgtgc tgtctctaga    4200
tgggagggta tgaaagttgt cgtgaatgcg ctggttcaag ctataccgtc catcttcaat    4260
gtgctattgg tgtgtctgat attttggctt attttttgcca ttatgggagt acagcttttt   4320
gctggaaaat attttaagtg taaagatggt aatgacactg tgctgagcca tgaaatcata    4380
ccgaatcgta atgcctgcaa aagtgaaaac tacacctggg aaaattcggc aatgaacttc    4440
gatcatgtag gtaatgcgta tctctgtcta tttcaagtgg ccacctttaa gggctggatc    4500
cagattatga acgatgccat tgattcacga gaggtggaca agcagccgat ccgagaaacc    4560
aatatctaca tgtatttata tttcgtattc ttcattatat ttggatcatt tttcacactc    4620
aatctgttca ttggtgttat cattgataat tttaatgaac aaaagaagaa agcaggtgga    4680
tcattagaaa tgttcatgac agaagatcag aaaaagtact ataatgctat gaaaagatg    4740 ggctctaaaa aaccattaaa agccattcca agaccgaggt ggcgaccaca agcaatagta    4800
ttcgaaatag ttacagataa aaaattcgat ataatcatta tgttgttcat ggcttaaac    4860 atgtttacca tgaccctcga tcggtacgac gcctccgagg cgtacaacaa tgtcctcgac    4920
aaactcaatg ggatattcgt agttattttc agtggcgaat gtctattaaa atatattcgct   4980 ttacgatatc actatttcaa agagccatgg aatttatttg atgtagtagt tgtcattta    5040 tccatccttag gtcttgtact cagcgacatc attgagaagt atttcgtatc gccgacactg   5100
ctccgtgtgg tgagagtggc caaagtgggt cgtgtcctgc gtttagtcaa gggtgccaag    5160
ggtatccgga cgttgctgtt cgcgttagcc atgtcgttgc ctgccttatt caacatttgt    5220
ctgttgctgt tcttggtgat gttcatcttt gctatctttg gcatgtcctt cttcatgcat    5280
gtcaaagaga gagcggcat aaatgctgtg tataatttta agacatttgg ccaaagtatg    5340
atattgctgt ttcagatgtc tacctcagcc ggttgggatg tgtgttaga tgccattatc    5400 aatgaggaag attgcgatcc acccgacaac gacaagggct atccgggcaa ttgtggttca    5460
gcgactgttg gaattacgtt tctcctttca tatctagtta aagcttttt gatagttatt    5520 aatatgtaca ttgctgtcat tctcgagaac tatagccagg ctacgaggga tgtacaggag    5580
ggtctcaccg acgacgacta tgatatgtac tacgagattt ggcaacaatt cgatccggag    5640
ggtacccagt acataagata cgaccagctg tccgagttcc tggacgtgct ggagccgccg    5700
ctgcagatcc acaagccgaa caagtacaaa atcatatcga tggacatgcc gatatgtcgg    5760
ggcgacatga tgtactgtgt ggatatattg gatgccctga ccaaggactt ctttgcgcgc    5820
aagggtaatc cgatcgagga cacgggtgaa attggtgaga ttgcggcgcg accggacacc    5880
gagggctatg atccggtgtc gtcgacactg tggcgccagc gtgaggagta ctgcgccaag    5940
ctgatacaga atgcgtggcg gcgttacaag aatggcccac cccaggaggg tgatgagggc    6000
gaggcggctg gtggcgaaga tggtgctgaa ggcggtgagg gtgaaggcgg cagcggcggc    6060
ggcggcgatg atgatggtgg ctcagcgacg gcggcgggaa ccacatcacc cacagatcca    6120
gatgccggcg aagcagatgg tgccagcgcc ggcaatggtg gcggcccccct tagtccgggc   6180 tgtgttagtg gcggcagtaa tggccgccaa acggccgtac tggtcgaaag cgatggtttt    6240
gttacaaaaa acggtcataa ggttgtaata cactcgagat cgccgagcat aacatccagg    6300
acggcagatg tctga                                                    6315

<210> SEQ ID NO 3
<211> LENGTH: 2105
<212> TYPE: PRT
<213> ORGANISM: Musca domestica
```

<400> SEQUENCE: 3

```
Met Thr Glu Asp Ser Asp Ser Ile Ser Glu Glu Arg Ser Leu Phe
  1               5                  10                  15

Arg Pro Phe Thr Arg Glu Ser Leu Leu Gln Ile Glu Gln Arg Ile Ala
                 20                  25                  30

Glu His Glu Lys Gln Lys Glu Leu Glu Arg Lys Arg Ala Ala Glu Gly
             35                  40                  45

Glu Gln Ile Arg Tyr Asp Asp Glu Asp Glu Asp Glu Gly Pro Gln Pro
         50                  55                  60

Asp Pro Thr Leu Glu Gln Gly Val Pro Ile Pro Val Arg Met Gln Gly
 65                  70                  75                  80

Ser Phe Pro Pro Glu Leu Ala Ser Thr Pro Leu Glu Asp Ile Asp Pro
                 85                  90                  95

Phe Tyr Ser Asn Val Leu Thr Phe Val Val Ile Ser Lys Gly Lys Asp
                100                 105                 110

Ile Phe Arg Phe Ser Ala Ser Lys Ala Met Trp Leu Leu Asp Pro Phe
            115                 120                 125

Asn Pro Ile Arg Arg Val Ala Ile Tyr Ile Leu Val His Pro Leu Phe
        130                 135                 140

Ser Leu Phe Ile Ile Thr Thr Ile Leu Thr Asn Cys Ile Leu Met Ile
145                 150                 155                 160

Met Pro Thr Thr Pro Thr Val Glu Ser Thr Glu Val Ile Phe Thr Gly
                165                 170                 175

Ile Tyr Thr Phe Glu Ser Ala Val Lys Val Met Ala Arg Gly Phe Ile
            180                 185                 190

Leu Cys Pro Phe Thr Tyr Leu Arg Asp Ala Trp Asn Trp Leu Asp Phe
        195                 200                 205

Val Val Ile Ala Leu Ala Tyr Val Thr Met Gly Ile Asp Leu Gly Asn
    210                 215                 220

Leu Ala Ala Leu Arg Thr Phe Arg Val Leu Arg Ala Leu Lys Thr Val
225                 230                 235                 240

Ala Ile Val Pro Gly Leu Lys Thr Ile Val Gly Ala Val Ile Glu Ser
                245                 250                 255

Val Lys Asn Leu Arg Asp Val Ile Ile Leu Thr Met Phe Ser Leu Ser
            260                 265                 270

Val Phe Ala Leu Met Gly Leu Gln Ile Tyr Met Gly Val Leu Thr Gln
        275                 280                 285

Lys Cys Ile Lys Arg Phe Pro Leu Asp Gly Ser Trp Gly Asn Leu Thr
    290                 295                 300

Asp Glu Asn Trp Phe Leu His Asn Ser Asn Ser Ser Asn Trp Phe Thr
305                 310                 315                 320

Glu Asn Asp Gly Glu Ser Tyr Pro Val Cys Gly Asn Val Ser Gly Ala
                325                 330                 335

Gly Gln Cys Gly Glu Asp Tyr Val Cys Leu Gln Gly Phe Gly Pro Asn
            340                 345                 350

Pro Asn Tyr Asp Tyr Thr Ser Phe Asp Ser Phe Gly Trp Ala Phe Leu
        355                 360                 365

Ser Ala Phe Arg Leu Met Thr Gln Asp Phe Trp Glu Asp Leu Tyr Gln
    370                 375                 380

His Val Leu Gln Ala Ala Gly Pro Trp His Met Leu Phe Phe Ile Val
385                 390                 395                 400

Ile Ile Phe Leu Gly Ser Phe Tyr Leu Val Asn Leu Ile Leu Ala Ile
```

-continued

```
                405                 410                 415
Val Ala Met Ser Tyr Asp Glu Leu Gln Lys Lys Ala Glu Glu Glu
            420                 425                 430
Ala Ala Glu Glu Glu Ala Ile Arg Glu Ala Glu Ala Ala Ala Ala
            435                 440                 445
Lys Ala Ala Lys Leu Glu Glu Arg Ala Asn Val Ala Ala Gln Ala Ala
            450                 455                 460
Gln Asp Ala Ala Asp Ala Ala Ala Ala Leu His Pro Glu Met Ala
465                 470                 475                 480
Lys Ser Pro Thr Tyr Ser Cys Ile Ser Tyr Glu Leu Phe Val Gly Gly
                485                 490                 495
Glu Lys Gly Asn Asp Asp Asn Asn Lys Glu Lys Met Ser Ile Arg Ser
            500                 505                 510
Val Glu Val Glu Ser Glu Ser Val Ser Val Ile Gln Arg Gln Pro Ala
            515                 520                 525
Pro Thr Thr Ala Pro Ala Thr Lys Val Arg Lys Val Ser Thr Thr Ser
            530                 535                 540
Leu Ser Leu Pro Gly Ser Pro Phe Asn Leu Arg Arg Gly Ser Arg Ser
545                 550                 555                 560
Ser His Lys Tyr Thr Ile Arg Asn Gly Arg Gly Arg Phe Gly Ile Pro
                565                 570                 575
Gly Ser Asp Arg Lys Pro Leu Val Leu Gln Thr Tyr Gln Asp Ala Gln
            580                 585                 590
Gln His Leu Pro Tyr Ala Asp Asp Ser Asn Ala Val Thr Pro Met Ser
            595                 600                 605
Glu Glu Asn Gly Ala Ile Ile Val Pro Ala Tyr Tyr Cys Asn Leu Gly
            610                 615                 620
Ser Arg His Ser Ser Tyr Thr Ser His Gln Ser Arg Ile Ser Tyr Thr
625                 630                 635                 640
Ser His Gly Asp Leu Leu Gly Gly Met Ala Ala Met Gly Ala Ser Thr
                645                 650                 655
Met Thr Lys Glu Ser Lys Leu Arg Ser Arg Asn Thr Arg Asn Gln Ser
            660                 665                 670
Ile Gly Ala Ala Thr Asn Gly Gly Ser Ser Thr Ala Gly Gly Gly Tyr
            675                 680                 685
Pro Asp Ala Asn His Lys Glu Gln Arg Asp Tyr Glu Met Gly Gln Asp
            690                 695                 700
Tyr Thr Asp Glu Ala Gly Lys Ile Lys His His Asp Asn Pro Phe Ile
705                 710                 715                 720
Glu Pro Val Gln Thr Gln Thr Val Val Asp Met Lys Asp Val Met Val
                725                 730                 735
Leu Asn Asp Ile Ile Glu Gln Ala Ala Gly Arg His Ser Arg Ala Ser
            740                 745                 750
Glu Arg Gly Glu Asp Asp Glu Asp Gly Pro Thr Phe Lys Asp Ile
            755                 760                 765
Ala Leu Glu Tyr Ile Leu Lys Gly Ile Glu Ile Phe Cys Val Trp Asp
            770                 775                 780
Cys Cys Trp Val Trp Leu Lys Phe Gln Glu Trp Val Ser Phe Ile Val
785                 790                 795                 800
Phe Asp Pro Phe Val Glu Leu Phe Ile Thr Leu Cys Ile Val Val Asn
                805                 810                 815
Thr Met Phe Met Ala Met Asp His His Asp Met Asn Pro Glu Leu Glu
            820                 825                 830
```

-continued

```
Lys Val Leu Lys Ser Gly Asn Tyr Phe Phe Thr Ala Thr Phe Ala Ile
            835                 840                 845
Glu Ala Ser Met Lys Leu Met Ala Met Ser Pro Lys Tyr Tyr Phe Gln
    850                 855                 860
Glu Gly Trp Asn Ile Phe Asp Phe Ile Ile Val Ala Leu Ser Leu Leu
865                 870                 875                 880
Glu Leu Gly Leu Glu Gly Val Gln Gly Leu Ser Val Leu Arg Ser Phe
                885                 890                 895
Arg Leu Leu Arg Val Phe Lys Leu Ala Lys Ser Trp Pro Thr Leu Asn
            900                 905                 910
Leu Leu Ile Ser Ile Met Gly Arg Thr Met Gly Ala Leu Gly Asn Leu
            915                 920                 925
Thr Phe Val Leu Cys Ile Ile Phe Ile Phe Ala Val Met Gly Met
            930                 935                 940
Gln Leu Phe Gly Lys Asn Tyr Ile Asp His Lys Asp Arg Phe Lys Asp
945                 950                 955                 960
His Glu Leu Pro Arg Trp Asn Phe Thr Asp Phe Met His Ser Phe Met
                965                 970                 975
Ile Val Phe Arg Val Leu Cys Gly Glu Trp Ile Glu Ser Met Trp Asp
            980                 985                 990
Cys Met Tyr Val Gly Asp Val Ser Cys Ile Pro Phe Phe Leu Ala Thr
            995                1000                1005
Val Val Ile Gly Asn Leu Val Val Leu Asn Leu Phe Leu Ala Leu Leu
           1010                1015                1020
Leu Ser Asn Phe Gly Ser Ser Ser Leu Ser Ala Pro Thr Ala Asp Asn
1025                1030                1035                1040
Asp Thr Asn Lys Ile Ala Glu Ala Phe Asn Arg Ile Ala Arg Phe Lys
                1045                1050                1055
Asn Trp Val Lys Arg Asn Ile Ala Asp Cys Phe Lys Leu Ile Arg Asn
            1060                1065                1070
Lys Leu Thr Asn Gln Ile Ser Asp Gln Pro Ser Glu His Gly Asp Asn
            1075                1080                1085
Glu Leu Glu Leu Gly His Asp Glu Ile Met Gly Asp Gly Leu Ile Lys
    1090                1095                1100
Lys Gly Met Lys Gly Glu Thr Gln Leu Glu Val Ala Ile Gly Asp Gly
1105                1110                1115                1120
Met Glu Phe Thr Ile His Gly Asp Met Lys Asn Asn Lys Pro Lys Lys
                1125                1130                1135
Ser Lys Phe Met Asn Asn Thr Thr Met Ile Gly Asn Ser Ile Asn His
            1140                1145                1150
Gln Asp Asn Arg Leu Glu His Glu Leu Asn His Arg Gly Leu Ser Ile
            1155                1160                1165
Gln Asp Asp Asp Thr Ala Ser Ile Asn Ser Tyr Gly Ser His Lys Asn
            1170                1175                1180
Arg Pro Phe Lys Asp Glu Ser His Lys Gly Ser Ala Glu Thr Ile Glu
1185                1190                1195                1200
Gly Glu Glu Lys Arg Asp Val Ser Lys Glu Asp Leu Gly Leu Asp Glu
                1205                1210                1215
Glu Leu Asp Glu Glu Ala Glu Gly Asp Glu Gly Gln Leu Asp Gly Asp
            1220                1225                1230
Ile Ile Ile His Ala Gln Asn Asp Asp Glu Ile Asp Asp Tyr Pro
            1235                1240                1245
```

```
Ala Asp Cys Phe Pro Asp Ser Tyr Tyr Lys Lys Phe Pro Ile Leu Ala
    1250                1255                1260

Gly Asp Glu Asp Ser Pro Phe Trp Gln Gly Trp Gly Asn Leu Arg Leu
1265                1270                1275                1280

Lys Thr Phe Gln Leu Ile Glu Asn Lys Tyr Phe Glu Thr Ala Val Ile
            1285                1290                1295

Thr Met Ile Leu Met Ser Ser Leu Ala Leu Ala Leu Glu Asp Val His
            1300                1305                1310

Leu Pro Asp Arg Pro Val Met Gln Asp Ile Leu Tyr Tyr Met Asp Arg
            1315                1320                1325

Ile Phe Thr Val Ile Phe Leu Glu Met Leu Ile Lys Trp Leu Ala
            1330                1335                1340

Leu Gly Phe Lys Val Tyr Phe Thr Asn Ala Trp Cys Trp Leu Asp Phe
1345                1350                1355                1360

Val Ile Val Met Leu Ser Leu Ile Asn Leu Val Ala Val Trp Ser Gly
                1365                1370                1375

Leu Asn Asp Ile Ala Val Phe Arg Ser Met Arg Thr Leu Arg Ala Leu
            1380                1385                1390

Arg Pro Leu Arg Ala Val Ser Arg Trp Glu Gly Met Lys Val Val Val
        1395                1400                1405

Asn Ala Leu Val Gln Ala Ile Pro Ser Ile Phe Asn Val Leu Leu Val
        1410                1415                1420

Cys Leu Ile Phe Trp Leu Ile Phe Ala Ile Met Gly Val Gln Leu Phe
1425                1430                1435                1440

Ala Gly Lys Tyr Phe Lys Cys Lys Asp Gly Asn Asp Thr Val Leu Ser
                1445                1450                1455

His Glu Ile Ile Pro Asn Arg Asn Ala Cys Lys Ser Glu Asn Tyr Thr
            1460                1465                1470

Trp Glu Asn Ser Ala Met Asn Phe Asp His Val Gly Asn Ala Tyr Leu
            1475                1480                1485

Cys Leu Phe Gln Val Ala Thr Phe Lys Gly Trp Ile Gln Ile Met Asn
        1490                1495                1500

Asp Ala Ile Asp Ser Arg Glu Val Asp Lys Gln Pro Ile Arg Glu Thr
1505                1510                1515                1520

Asn Ile Tyr Met Tyr Leu Tyr Phe Val Phe Phe Ile Ile Phe Gly Ser
            1525                1530                1535

Phe Phe Thr Leu Asn Leu Phe Ile Gly Val Ile Ile Asp Asn Phe Asn
            1540                1545                1550

Glu Gln Lys Lys Lys Ala Gly Gly Ser Leu Glu Met Phe Met Thr Glu
        1555                1560                1565

Asp Gln Lys Lys Tyr Tyr Asn Ala Met Lys Lys Met Gly Ser Lys Lys
    1570                1575                1580

Pro Leu Lys Ala Ile Pro Arg Pro Arg Trp Arg Pro Gln Ala Ile Val
1585                1590                1595                1600

Phe Glu Ile Val Thr Asp Lys Lys Phe Asp Ile Ile Ile Met Leu Phe
            1605                1610                1615

Ile Gly Leu Asn Met Phe Thr Met Thr Leu Asp Arg Tyr Asp Ala Ser
            1620                1625                1630

Glu Ala Tyr Asn Asn Val Leu Asp Lys Leu Asn Gly Ile Phe Val Val
            1635                1640                1645

Ile Phe Ser Gly Glu Cys Leu Leu Lys Ile Phe Ala Leu Arg Tyr His
        1650                1655                1660

Tyr Phe Lys Glu Pro Trp Asn Leu Phe Asp Val Val Val Val Ile Leu
```

-continued

```
            1665                1670                1675                1680

Ser Ile Leu Gly Leu Val Leu Ser Asp Ile Ile Glu Lys Tyr Phe Val
                    1685                1690                1695

Ser Pro Thr Leu Leu Arg Val Val Arg Val Ala Lys Val Gly Arg Val
                    1700                1705                1710

Leu Arg Leu Val Lys Gly Ala Lys Gly Ile Arg Thr Leu Leu Phe Ala
                    1715                1720                1725

Leu Ala Met Ser Leu Pro Ala Leu Phe Asn Ile Cys Leu Leu Leu Phe
                    1730                1735                1740

Leu Val Met Phe Ile Phe Ala Ile Phe Gly Met Ser Phe Phe Met His
1745                1750                1755                1760

Val Lys Glu Lys Ser Gly Ile Asn Ala Val Tyr Asn Phe Lys Thr Phe
                    1765                1770                1775

Gly Gln Ser Met Ile Leu Leu Phe Gln Met Ser Thr Ser Ala Gly Trp
                    1780                1785                1790

Asp Gly Val Leu Asp Ala Ile Ile Asn Glu Asp Cys Asp Pro Pro
                    1795                1800                1805

Asp Asn Asp Lys Gly Tyr Pro Gly Asn Cys Gly Ser Ala Thr Val Gly
                    1810                1815                1820

Ile Thr Phe Leu Leu Ser Tyr Leu Val Ile Ser Phe Leu Ile Val Ile
1825                1830                1835                1840

Asn Met Tyr Ile Ala Val Ile Leu Glu Asn Tyr Ser Gln Ala Thr Glu
                    1845                1850                1855

Asp Val Gln Glu Gly Leu Thr Asp Asp Tyr Asp Met Tyr Tyr Glu
                    1860                1865                1870

Ile Trp Gln Gln Phe Asp Pro Glu Gly Thr Gln Tyr Ile Arg Tyr Asp
                    1875                1880                1885

Gln Leu Ser Glu Phe Leu Asp Val Leu Glu Pro Pro Leu Gln Ile His
                    1890                1895                1900

Lys Pro Asn Lys Tyr Lys Ile Ile Ser Met Asp Met Pro Ile Cys Arg
1905                1910                1915                1920

Gly Asp Met Met Tyr Cys Val Asp Ile Leu Asp Ala Leu Thr Lys Asp
                    1925                1930                1935

Phe Phe Ala Arg Lys Gly Asn Pro Ile Glu Glu Thr Gly Glu Ile Gly
                    1940                1945                1950

Glu Ile Ala Ala Arg Pro Asp Thr Glu Gly Tyr Asp Pro Val Ser Ser
                    1955                1960                1965

Thr Leu Trp Arg Gln Arg Glu Glu Tyr Cys Ala Lys Leu Ile Gln Asn
                    1970                1975                1980

Ala Trp Arg Arg Tyr Lys Asn Gly Pro Pro Gln Glu Gly Asp Glu Gly
1985                1990                1995                2000

Glu Ala Ala Gly Gly Glu Asp Gly Ala Glu Gly Glu Gly Glu Gly
                    2005                2010                2015

Gly Ser Gly Gly Gly Gly Asp Asp Gly Gly Ser Ala Thr Gly Ala
                    2020                2025                2030

Thr Ala Ala Gly Ala Thr Ser Pro Ser Asp Pro Asp Ala Gly Glu
                    2035                2040                2045

Ala Asp Gly Ala Ser Val Gly Gly Pro Leu Ser Pro Gly Cys Val Ser
2050                2055                2060

Gly Gly Ser Asn Gly Arg Gln Thr Ala Val Leu Val Glu Ser Asp Gly
2065                2070                2075                2080

Phe Val Thr Lys Asn Gly His Lys Val Val Ile His Ser Arg Ser Pro
                    2085                2090                2095
```

Ser Ile Thr Ser Arg Thr Ala Asp Val
            2100                2105

<210> SEQ ID NO 4
<211> LENGTH: 2104
<212> TYPE: PRT
<213> ORGANISM: Musca domestica

<400> SEQUENCE: 4

Met Thr Glu Asp Ser Asp Ser Ile Ser Glu Glu Arg Ser Leu Phe
 1               5                  10                  15

Arg Pro Phe Thr Arg Glu Ser Leu Leu Gln Ile Glu Gln Arg Ile Ala
                20                  25                  30

Glu His Glu Lys Gln Lys Glu Leu Glu Arg Lys Arg Ala Ala Glu Gly
            35                  40                  45

Glu Gln Ile Arg Tyr Asp Asp Glu Asp Glu Asp Glu Gly Pro Gln Pro
        50                  55                  60

Asp Pro Thr Leu Glu Gln Gly Val Pro Ile Pro Val Arg Met Gln Gly
 65                  70                  75                  80

Ser Phe Pro Pro Glu Leu Ala Ser Thr Pro Leu Glu Asp Ile Asp Pro
                85                  90                  95

Phe Tyr Ser Asn Val Leu Thr Phe Val Val Ile Ser Lys Gly Lys Asp
                100                 105                 110

Ile Phe Arg Phe Ser Ala Ser Lys Ala Met Trp Leu Leu Asp Pro Phe
            115                 120                 125

Asn Pro Ile Arg Arg Val Ala Ile Tyr Ile Leu Val His Pro Leu Phe
        130                 135                 140

Ser Leu Phe Ile Ile Thr Thr Ile Leu Thr Asn Cys Ile Leu Met Ile
145                 150                 155                 160

Met Pro Thr Thr Pro Thr Val Glu Ser Thr Glu Val Ile Phe Thr Gly
                165                 170                 175

Ile Tyr Thr Phe Glu Ser Ala Val Lys Val Met Ala Arg Gly Phe Ile
            180                 185                 190

Leu Cys Pro Phe Thr Tyr Leu Arg Asp Ala Trp Asn Trp Leu Asp Phe
        195                 200                 205

Val Val Ile Ala Leu Ala Tyr Val Thr Met Gly Ile Asp Leu Gly Asn
        210                 215                 220

Leu Ala Ala Leu Arg Thr Phe Arg Val Leu Arg Ala Leu Lys Thr Val
225                 230                 235                 240

Ala Ile Val Pro Gly Leu Lys Thr Ile Val Gly Ala Val Ile Glu Ser
                245                 250                 255

Val Lys Asn Leu Arg Asp Val Ile Ile Leu Thr Met Phe Ser Leu Ser
            260                 265                 270

Val Phe Ala Leu Met Gly Leu Gln Ile Tyr Met Gly Val Leu Thr Gln
        275                 280                 285

Lys Cys Ile Lys Arg Phe Pro Leu Asp Gly Ser Trp Gly Asn Leu Thr
        290                 295                 300

Asp Glu Asn Trp Phe Leu His Asn Ser Asn Ser Asn Trp Phe Thr
305                 310                 315                 320

Glu Asn Asp Gly Glu Ser Tyr Pro Val Cys Gly Asn Val Ser Gly Ala
                325                 330                 335

Gly Gln Cys Gly Glu Asp Tyr Val Cys Leu Gln Gly Phe Gly Pro Asn
            340                 345                 350

Pro Asn Tyr Asp Tyr Thr Ser Phe Asp Ser Phe Gly Trp Ala Phe Leu

-continued

```
                355                 360                 365
Ser Ala Phe Arg Leu Met Thr Gln Asp Phe Trp Glu Asp Leu Tyr Gln
        370                 375                 380

His Val Leu Gln Ala Ala Gly Pro Trp His Met Leu Phe Phe Ile Val
385                 390                 395                 400

Ile Ile Phe Leu Gly Ser Phe Tyr Leu Val Asn Leu Ile Leu Ala Ile
                405                 410                 415

Val Ala Met Ser Tyr Asp Glu Leu Gln Lys Lys Ala Glu Glu Glu Glu
                420                 425                 430

Ala Ala Glu Glu Glu Ala Ile Arg Glu Ala Glu Ala Ala Ala Ala Ala
        435                 440                 445

Lys Ala Ala Lys Leu Glu Glu Arg Ala Asn Val Ala Ala Gln Ala Ala
450                 455                 460

Gln Asp Ala Ala Asp Ala Ala Ala Ala Leu His Pro Glu Met Ala
465                 470                 475                 480

Lys Ser Pro Thr Tyr Ser Cys Ile Ser Tyr Glu Leu Phe Val Gly Gly
                485                 490                 495

Glu Lys Gly Asn Asp Asp Asn Asn Lys Glu Lys Met Ser Ile Arg Ser
                500                 505                 510

Val Glu Val Glu Ser Glu Ser Val Ser Val Ile Gln Arg Gln Pro Ala
        515                 520                 525

Pro Thr Thr Ala Pro Ala Thr Lys Val Arg Lys Val Ser Thr Thr Ser
        530                 535                 540

Leu Ser Leu Pro Gly Ser Pro Phe Asn Leu Arg Arg Gly Ser Arg Ser
545                 550                 555                 560

Ser His Lys Tyr Thr Ile Arg Asn Gly Arg Gly Arg Phe Gly Ile Pro
                565                 570                 575

Gly Ser Asp Arg Lys Pro Leu Val Leu Gln Thr Tyr Gln Asp Ala Gln
                580                 585                 590

Gln His Leu Pro Tyr Ala Asp Asp Ser Asn Ala Val Thr Pro Met Ser
                595                 600                 605

Glu Glu Asn Gly Ala Ile Ile Val Pro Ala Tyr Tyr Cys Asn Leu Gly
        610                 615                 620

Ser Arg His Ser Ser Tyr Thr Ser His Gln Ser Arg Ile Ser Tyr Thr
625                 630                 635                 640

Ser His Gly Asp Leu Leu Gly Gly Met Ala Ala Met Gly Ala Ser Thr
                645                 650                 655

Met Thr Lys Glu Ser Lys Leu Arg Ser Arg Asn Thr Arg Asn Gln Ser
                660                 665                 670

Ile Gly Ala Ala Thr Asn Gly Gly Ser Ser Thr Ala Gly Gly Gly Tyr
        675                 680                 685

Pro Asp Ala Asn His Lys Glu Gln Arg Asp Tyr Glu Met Gly Gln Asp
690                 695                 700

Tyr Thr Asp Glu Ala Gly Lys Ile Lys His His Asp Asn Pro Phe Ile
705                 710                 715                 720

Glu Pro Val Gln Thr Gln Thr Val Val Asp Met Lys Asp Val Met Val
                725                 730                 735

Leu Asn Asp Ile Ile Glu Gln Ala Ala Gly Arg His Ser Arg Ala Ser
                740                 745                 750

Glu Arg Gly Glu Asp Asp Asp Glu Asp Gly Pro Thr Phe Lys Asp Ile
        755                 760                 765

Ala Leu Glu Tyr Ile Leu Lys Gly Ile Glu Ile Phe Cys Val Trp Asp
770                 775                 780
```

-continued

```
Cys Cys Trp Val Trp Leu Lys Phe Gln Glu Trp Val Ser Phe Ile Val
785                 790                 795                 800

Phe Asp Pro Phe Val Glu Leu Phe Ile Thr Leu Cys Ile Val Val Asn
                805                 810                 815

Thr Met Phe Met Ala Met Asp His His Asp Met Asn Pro Glu Leu Glu
                820                 825                 830

Lys Val Leu Lys Ser Gly Asn Tyr Phe Phe Thr Ala Thr Phe Ala Ile
                835                 840                 845

Glu Ala Ser Met Lys Leu Met Ala Met Ser Pro Lys Tyr Tyr Phe Gln
850                 855                 860

Glu Gly Trp Asn Ile Phe Asp Phe Ile Ile Val Ala Leu Ser Leu Leu
865                 870                 875                 880

Glu Leu Gly Leu Glu Gly Val Gln Gly Leu Ser Val Leu Arg Ser Phe
                885                 890                 895

Arg Leu Leu Arg Val Phe Lys Leu Ala Lys Ser Trp Pro Thr Leu Asn
                900                 905                 910

Leu Leu Ile Ser Ile Met Gly Arg Thr Met Gly Ala Leu Gly Asn Leu
                915                 920                 925

Thr Phe Val Leu Cys Ile Ile Ile Phe Ile Phe Ala Val Met Gly Met
                930                 935                 940

Gln Leu Phe Gly Lys Asn Tyr Ile Asp His Lys Asp Arg Phe Lys Asp
945                 950                 955                 960

His Glu Leu Pro Arg Trp Asn Phe Thr Asp Phe Met His Ser Phe Met
                965                 970                 975

Ile Val Phe Arg Val Leu Cys Gly Glu Trp Ile Glu Ser Met Trp Asp
                980                 985                 990

Cys Met Tyr Val Gly Asp Val Ser Cys Ile Pro Phe Phe Leu Ala Thr
                995                 1000                1005

Val Val Ile Gly Asn Phe Val Val Leu Asn Leu Phe Leu Ala Leu Leu
                1010                1015                1020

Leu Ser Asn Phe Gly Ser Ser Ser Leu Ser Ala Pro Thr Ala Asp Asn
1025                1030                1035                1040

Asp Thr Asn Lys Ile Ala Glu Ala Phe Asn Arg Ile Ala Arg Phe Lys
                1045                1050                1055

Asn Trp Val Lys Arg Asn Ile Ala Asp Cys Phe Lys Leu Ile Arg Asn
                1060                1065                1070

Lys Leu Thr Asn Gln Ile Ser Asp Gln Pro Ser Glu His Gly Asp Asn
                1075                1080                1085

Glu Leu Glu Leu Gly His Asp Glu Ile Met Gly Asp Gly Leu Ile Lys
                1090                1095                1100

Lys Gly Met Lys Gly Glu Thr Gln Leu Glu Val Ala Ile Gly Asp Gly
1105                1110                1115                1120

Met Glu Phe Thr Ile His Gly Asp Met Lys Asn Asn Lys Pro Lys Lys
                1125                1130                1135

Ser Lys Phe Ile Asn Asn Thr Thr Met Ile Gly Asn Ser Ile Asn His
                1140                1145                1150

Gln Asp Asn Arg Leu Glu His Glu Leu Asn His Arg Gly Leu Ser Ile
                1155                1160                1165

Gln Asp Asp Asp Thr Ala Ser Ile Asn Ser Tyr Gly Ser His Lys Asn
                1170                1175                1180

Arg Pro Phe Lys Asp Glu Ser His Lys Gly Ser Ala Glu Thr Ile Glu
1185                1190                1195                1200
```

-continued

Gly Glu Glu Lys Arg Asp Val Ser Lys Glu Asp Leu Gly Leu Asp Glu
            1205                1210                1215

Glu Leu Asp Glu Glu Ala Gly Asp Glu Gly Gln Leu Asp Gly Asp
            1220                1225                1230

Ile Ile Ile His Ala Gln Asn Asp Asp Glu Ile Ile Asp Asp Tyr Pro
            1235                1240                1245

Ala Asp Cys Phe Pro Asp Ser Tyr Tyr Lys Lys Phe Pro Ile Leu Ala
            1250                1255                1260

Gly Asp Glu Asp Ser Pro Phe Trp Gln Gly Trp Gly Asn Leu Arg Leu
1265                1270                1275                1280

Lys Thr Phe Gln Leu Ile Glu Asn Lys Tyr Phe Glu Thr Ala Val Ile
            1285                1290                1295

Thr Met Ile Leu Met Ser Ser Leu Ala Leu Ala Leu Glu Asp Val His
            1300                1305                1310

Leu Pro Asp Arg Pro Val Met Gln Asp Ile Leu Tyr Tyr Met Asp Arg
            1315                1320                1325

Ile Phe Thr Val Ile Phe Phe Leu Glu Met Leu Ile Lys Trp Leu Ala
            1330                1335                1340

Leu Gly Phe Lys Val Tyr Phe Thr Asn Ala Trp Cys Trp Leu Asp Phe
1345                1350                1355                1360

Val Ile Val Met Leu Ser Leu Ile Asn Leu Val Ala Val Trp Ser Gly
            1365                1370                1375

Leu Asn Asp Ile Ala Val Phe Arg Ser Met Arg Thr Leu Arg Ala Leu
            1380                1385                1390

Arg Pro Leu Arg Ala Val Ser Arg Trp Glu Gly Met Lys Val Val Val
            1395                1400                1405

Asn Ala Leu Val Gln Ala Ile Pro Ser Ile Phe Asn Val Leu Leu Val
            1410                1415                1420

Cys Leu Ile Phe Trp Leu Ile Phe Ala Ile Met Gly Val Gln Leu Phe
1425                1430                1435                1440

Ala Gly Lys Tyr Phe Lys Cys Lys Asp Gly Asn Asp Thr Val Leu Ser
            1445                1450                1455

His Glu Ile Ile Pro Asn Arg Asn Ala Cys Lys Ser Glu Asn Tyr Thr
            1460                1465                1470

Trp Glu Asn Ser Ala Met Asn Phe Asp His Val Gly Asn Ala Tyr Leu
            1475                1480                1485

Cys Leu Phe Gln Val Ala Thr Phe Lys Gly Trp Ile Gln Ile Met Asn
            1490                1495                1500

Asp Ala Ile Asp Ser Arg Glu Val Asp Lys Gln Pro Ile Arg Glu Thr
1505                1510                1515                1520

Asn Ile Tyr Met Tyr Leu Tyr Phe Val Phe Phe Ile Ile Phe Gly Ser
            1525                1530                1535

Phe Phe Thr Leu Asn Leu Phe Ile Gly Val Ile Ile Asp Asn Phe Asn
            1540                1545                1550

Glu Gln Lys Lys Lys Ala Gly Gly Ser Leu Glu Met Phe Met Thr Glu
            1555                1560                1565

Asp Gln Lys Lys Tyr Tyr Asn Ala Met Lys Lys Met Gly Ser Lys Lys
            1570                1575                1580

Pro Leu Lys Ala Ile Pro Arg Pro Arg Trp Arg Pro Gln Ala Ile Val
1585                1590                1595                1600

Phe Glu Ile Val Thr Asp Lys Lys Phe Asp Ile Ile Ile Met Leu Phe
            1605                1610                1615

Ile Gly Leu Asn Met Phe Thr Met Thr Leu Asp Arg Tyr Asp Ala Ser

-continued

```
              1620             1625             1630
Glu Ala Tyr Asn Asn Val Leu Asp Lys Leu Asn Gly Ile Phe Val Val
         1635             1640             1645
Ile Phe Ser Gly Glu Cys Leu Leu Lys Ile Phe Ala Leu Arg Tyr His
1650             1655             1660
Tyr Phe Lys Glu Pro Trp Asn Leu Phe Asp Val Val Val Ile Leu
1665             1670             1675             1680
Ser Ile Leu Gly Leu Val Leu Ser Asp Ile Ile Glu Lys Tyr Phe Val
              1685             1690             1695
Ser Pro Thr Leu Leu Arg Val Val Arg Val Ala Lys Val Gly Arg Val
         1700             1705             1710
Leu Arg Leu Val Lys Gly Ala Lys Gly Ile Arg Thr Leu Leu Phe Ala
         1715             1720             1725
Leu Ala Met Ser Leu Pro Ala Leu Phe Asn Ile Cys Leu Leu Leu Phe
         1730             1735             1740
Leu Val Met Phe Ile Phe Ala Ile Phe Gly Met Ser Phe Phe Met His
1745             1750             1755             1760
Val Lys Glu Lys Ser Gly Ile Asn Ala Val Tyr Asn Phe Lys Thr Phe
              1765             1770             1775
Gly Gln Ser Met Ile Leu Leu Phe Gln Met Ser Thr Ser Ala Gly Trp
         1780             1785             1790
Asp Gly Val Leu Asp Ala Ile Ile Asn Glu Glu Asp Cys Asp Pro Pro
         1795             1800             1805
Asp Asn Asp Lys Gly Tyr Pro Gly Asn Cys Gly Ser Ala Thr Val Gly
         1810             1815             1820
Ile Thr Phe Leu Leu Ser Tyr Leu Val Ile Ser Phe Leu Ile Val Ile
1825             1830             1835             1840
Asn Met Tyr Ile Ala Val Ile Leu Glu Asn Tyr Ser Gln Ala Thr Glu
              1845             1850             1855
Asp Val Gln Glu Gly Leu Thr Asp Asp Asp Tyr Asp Met Tyr Tyr Glu
         1860             1865             1870
Ile Trp Gln Gln Phe Asp Pro Glu Gly Thr Gln Tyr Ile Arg Tyr Asp
         1875             1880             1885
Gln Leu Ser Glu Phe Leu Asp Val Leu Glu Pro Pro Leu Gln Ile His
         1890             1895             1900
Lys Pro Asn Lys Tyr Lys Ile Ile Ser Met Asp Met Pro Ile Cys Arg
1905             1910             1915             1920
Gly Asp Met Met Tyr Cys Val Asp Ile Leu Asp Ala Leu Thr Lys Asp
              1925             1930             1935
Phe Phe Ala Arg Lys Gly Asn Pro Ile Glu Glu Thr Gly Glu Ile Gly
         1940             1945             1950
Glu Ile Ala Ala Arg Pro Asp Thr Glu Gly Tyr Asp Pro Val Ser Ser
         1955             1960             1965
Thr Leu Trp Arg Gln Arg Glu Glu Tyr Cys Ala Lys Leu Ile Gln Asn
         1970             1975             1980
Ala Trp Arg Arg Tyr Lys Asn Gly Pro Pro Gln Glu Gly Asp Glu Gly
1985             1990             1995             2000
Glu Ala Ala Gly Gly Glu Asp Gly Ala Glu Gly Glu Gly Glu Gly
              2005             2010             2015
Gly Ser Gly Gly Gly Gly Asp Asp Gly Gly Ser Ala Thr Ala Ala
              2020             2025             2030
Gly Ala Thr Ser Pro Thr Asp Pro Asp Ala Gly Glu Ala Asp Gly Ala
              2035             2040             2045
```

```
Ser Ala Gly Asn Gly Gly Pro Leu Ser Pro Gly Cys Val Ser Gly
    2050                2055                2060

Gly Ser Asn Gly Arg Gln Thr Ala Val Leu Val Glu Ser Asp Gly Phe
2065                2070                2075                2080

Val Thr Lys Asn Gly His Lys Val Val Ile His Ser Arg Ser Pro Ser
                2085                2090                2095

Ile Thr Ser Arg Thr Ala Asp Val
        2100
```

```
<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.

<400> SEQUENCE: 5
cggttgggct ttcctgtc                                                18

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.
<220> FEATURE:
<221> NAME/KEY: unsure
<222> LOCATION: (21)
<223> OTHER INFORMATION: N at position 21 is either A, C, G, or T

<400> SEQUENCE: 6
gggaattcra adatrttcca nccytc                                       26

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.
<220> FEATURE:
<221> NAME/KEY: unsure
<222> LOCATION: (18)
<223> OTHER INFORMATION: N at position 18 is either A, C, G, or T

<400> SEQUENCE: 7
cccgargaya thgaycynta yta                                          23

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.

<400> SEQUENCE: 8
cgtatcgcct cctcctcg                                                18

<210> SEQ ID NO 9
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      primers for PCR amplification of Vssc1 cDNAs.
<220> FEATURE:
<221> NAME/KEY: unsure
<222> LOCATION: (17)
<223> OTHER INFORMATION: N at any position in this sequence is A, C, G,
      or T

<400> SEQUENCE: 9
gggtctagat httygcnath ttyggnatg                                   29

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.
<220> FEATURE:
<221> NAME/KEY: unsure
<222> LOCATION: (10)
<223> OTHER INFORMATION: N at position 10 is either A, C, G, or T

<400> SEQUENCE: 10
ggggaattcn ggrtcraayt gytgcca                                     27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.
<220> FEATURE:
<221> NAME/KEY: unsure
<222> LOCATION: (13)
<223> OTHER INFORMATION: N at position 13 is either A, C, G, or T

<400> SEQUENCE: 11
gggtctagar gancaraara artayta                                     27

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.

<400> SEQUENCE: 12
tcatactttg gcccaatgtc                                             20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.

<400> SEQUENCE: 13
cccgaattag agaaggtgct g                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
``` primers for PCR amplification of Vssc1 cDNAs.

<400> SEQUENCE: 14
actattgctt gtggtcgcca c                                          21

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.
<220> FEATURE:
<221> NAME/KEY: unsure
<222> LOCATION: (5)
<223> OTHER INFORMATION: N at any position in this sequence is A, C, G,
      or T

<400> SEQUENCE: 15
catcnttrgc ngcntagacn atgac                                      25

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.

<400> SEQUENCE: 16
gattgaatgg atcgagcagc c                                          21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.

<400> SEQUENCE: 17
cgtttctcct ttcatatcta g                                          21

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primers for PCR amplification of Vssc1 cDNAs.
<220> FEATURE:
<221> NAME/KEY: unsure
<222> LOCATION: (11)
<223> OTHER INFORMATION: N at any position in this sequence is A, C, G,
      or T

<400> SEQUENCE: 18
ggagbggbgg nckbggnckn gctca                                      25

<210> SEQ ID NO 19
<211> LENGTH: 2100
<212> TYPE: PRT
<213> ORGANISM: Drosophila melanogaster

<400> SEQUENCE: 19

Met Thr Glu Asp Ser Asp Ser Ile Ser Glu Glu Glu Arg Ser Leu Phe
 1               5                  10                  15

-continued

```
Arg Pro Phe Thr Arg Glu Ser Leu Val Gln Ile Glu Gln Arg Ile Ala
            20                  25                  30

Ala Glu His Glu Lys Gln Lys Glu Leu Glu Arg Lys Arg Ala Glu Gly
            35                  40                  45

Glu Val Pro Arg Tyr Gly Arg Lys Lys Gln Lys Glu Ile Arg Tyr
        50                  55                  60

Asp Asp Glu Asp Glu Asp Glu Gly Pro Gln Pro Asp Pro Thr Leu Glu
65              70                  75                  80

Gln Gly Val Pro Ile Pro Val Arg Leu Gln Gly Ser Phe Pro Pro Glu
                85                  90                  95

Leu Ala Ser Thr Pro Leu Glu Asp Ile Asp Pro Tyr Tyr Ser Asn Val
            100                 105                 110

Leu Thr Phe Val Val Val Ser Lys Gly Lys Asp Ile Phe Arg Phe Ser
            115                 120                 125

Ala Ser Lys Ala Met Trp Met Leu Asp Pro Phe Asn Pro Ile Arg Arg
130                 135                 140

Val Ala Ile Tyr Ile Leu Val His Pro Leu Phe Ser Leu Phe Ile Ile
145                 150                 155                 160

Thr Thr Ile Leu Val Asn Cys Ile Leu Met Ile Met Pro Thr Thr Pro
                165                 170                 175

Thr Val Glu Ser Thr Glu Val Ile Phe Thr Gly Ile Tyr Thr Phe Glu
            180                 185                 190

Ser Ala Val Lys Val Met Ala Arg Gly Phe Ile Leu Cys Pro Phe Thr
            195                 200                 205

Tyr Leu Arg Asp Ala Trp Asn Trp Leu Asp Phe Val Val Ile Ala Leu
        210                 215                 220

Ala Tyr Val Thr Met Gly Ile Asp Leu Gly Asn Leu Ala Ala Leu Arg
225                 230                 235                 240

Thr Phe Arg Val Leu Arg Ala Leu Lys Thr Val Ala Ile Val Pro Gly
            245                 250                 255

Leu Lys Thr Ile Val Gly Ala Val Ile Glu Ser Val Lys Asn Leu Arg
            260                 265                 270

Asp Val Ile Ile Leu Thr Met Phe Ser Leu Ser Val Phe Ala Leu Met
            275                 280                 285

Gly Leu Gln Ile Tyr Met Gly Val Leu Thr Glu Lys Cys Ile Lys Lys
        290                 295                 300

Phe Pro Leu Asp Gly Ser Trp Gly Asn Leu Thr Asp Glu Asn Trp Asp
305                 310                 315                 320

Tyr His Asn Arg Asn Ser Ser Asn Trp Tyr Ser Glu Asp Glu Gly Ile
            325                 330                 335

Ser Phe Pro Leu Cys Gly Asn Ile Ser Gly Ala Gly Gln Cys Asp Asp
            340                 345                 350

Asp Tyr Val Cys Leu Gln Gly Phe Gly Pro Asn Pro Asn Tyr Gly Tyr
        355                 360                 365

Thr Ser Phe Asp Ser Phe Gly Trp Ala Phe Leu Ser Ala Phe Arg Leu
370                 375                 380

Met Thr Gln Asp Phe Trp Glu Asp Leu Tyr Gln Leu Val Leu Arg Ala
385                 390                 395                 400

Ala Gly Pro Trp His Met Leu Phe Phe Ile Val Ile Ile Phe Leu Gly
                405                 410                 415

Ser Phe Tyr Leu Val Asn Leu Ile Leu Ala Ile Val Ala Met Ser Tyr
            420                 425                 430

Asp Glu Leu Gln Arg Lys Ala Glu Glu Glu Ala Ala Glu Glu Glu
```

-continued

```
            435                 440                 445
Ala Ile Arg Glu Ala Glu Ala Ala Ala Lys Ala Ala Lys Leu
    450                 455                 460

Glu Glu Arg Ala Asn Ala Gln Ala Gln Ala Ala Asp Ala Ala
465                 470                 475                 480

Ala Glu Glu Ala Ala Leu His Pro Glu Met Ala Lys Ser Pro Thr Tyr
                    485                 490                 495

Ser Cys Ile Ser Tyr Glu Leu Phe Val Gly Gly Lys Gly Asn Asp
                    500                 505                 510

Asp Asn Asn Lys Glu Lys Met Ser Ile Arg Ser Val Glu Val Glu Ser
            515                 520                 525

Glu Ser Val Ser Val Ile Gln Arg Gln Pro Ala Pro Thr Thr Ala His
    530                 535                 540

Gln Ala Thr Lys Val Arg Lys Val Ser Thr Thr Ser Leu Ser Leu Pro
545                 550                 555                 560

Gly Ser Pro Phe Asn Ile Arg Arg Gly Ser Arg Ser Ser His Lys Tyr
                    565                 570                 575

Thr Ile Arg Asn Gly Arg Gly Arg Phe Gly Ile Pro Gly Ser Asp Arg
                    580                 585                 590

Lys Pro Leu Val Leu Ser Thr Tyr Gln Asp Ala Gln Gln His Leu Pro
                    595                 600                 605

Tyr Ala Asp Asp Ser Asn Ala Val Thr Pro Met Ser Glu Glu Asn Gly
                    610                 615                 620

Ala Ile Ile Val Pro Val Tyr Tyr Gly Asn Leu Gly Ser Arg His Ser
625                 630                 635                 640

Ser Tyr Thr Ser His Gln Ser Arg Ile Ser Tyr Thr Ser His Gly Asp
                    645                 650                 655

Leu Leu Gly Gly Met Ala Val Met Gly Val Ser Thr Met Thr Lys Glu
                    660                 665                 670

Ser Lys Leu Arg Asn Arg Asn Thr Arg Asn Gln Ser Val Gly Ala Thr
                    675                 680                 685

Asn Gly Gly Thr Thr Cys Leu Asp Thr Asn His Lys Leu Asp His Arg
690                 695                 700

Asp Tyr Glu Ile Gly Leu Glu Cys Thr Asp Glu Ala Gly Lys Ile Lys
705                 710                 715                 720

His His Asp Asn Pro Phe Ile Glu Pro Val Gln Thr Gln Thr Val Val
                    725                 730                 735

Asp Met Lys Asp Val Met Val Leu Asn Asp Ile Ile Glu Gln Ala Ala
            740                 745                 750

Gly Arg His Ser Arg Ala Ser Asp Arg Gly Glu Asp Asp Glu Asp
    755                 760                 765

Gly Pro Thr Phe Lys Asp Lys Ala Leu Glu Val Ile Leu Lys Gly Ile
770                 775                 780

Asp Val Phe Cys Val Trp Asp Cys Cys Trp Val Trp Leu Lys Phe Gln
785                 790                 795                 800

Glu Trp Val Ser Leu Ile Val Phe Asp Pro Phe Val Glu Leu Phe Ile
                    805                 810                 815

Thr Leu Cys Ile Val Val Asn Thr Met Phe Met Ala Met Asp His His
                    820                 825                 830

Asp Met Asn Lys Glu Met Glu Arg Val Leu Lys Ser Gly Asn Tyr Phe
            835                 840                 845

Phe Thr Ala Thr Phe Ala Ile Glu Ala Thr Met Lys Leu Met Ala Met
850                 855                 860
```

-continued

```
Ser Pro Lys Tyr Tyr Phe Gln Glu Gly Trp Asn Ile Phe Asp Phe Ile
865                 870                 875                 880

Ile Val Ala Leu Ser Leu Leu Glu Leu Gly Leu Glu Gly Val Gln Gly
                885                 890                 895

Leu Ser Val Leu Arg Ser Phe Arg Leu Leu Arg Val Phe Lys Leu Ala
                900                 905                 910

Lys Ser Trp Pro Thr Leu Asn Leu Leu Ile Ser Ile Met Gly Arg Thr
                915                 920                 925

Met Gly Ala Leu Gly Asn Leu Thr Phe Val Leu Cys Ile Ile Ile Phe
            930                 935                 940

Ile Phe Ala Val Met Gly Met Gln Leu Phe Gly Lys Asn Tyr His Asp
945                 950                 955                 960

His Lys Asp Arg Phe Pro Asp Gly Asp Leu Pro Arg Trp Asn Phe Thr
                965                 970                 975

Asp Phe Met His Ser Phe Met Ile Val Phe Arg Val Leu Cys Gly Glu
                980                 985                 990

Trp Ile Glu Ser Met Trp Asp Cys Met Tyr Val Gly Asp Val Ser Cys
                995                 1000                1005

Ile Pro Phe Phe Leu Ala Thr Val Val Ile Gly Asn Leu Val Val Leu
            1010                1015                1020

Asn Leu Phe Leu Ala Leu Leu Leu Ser Asn Phe Gly Ser Ser Ser Leu
1025                1030                1035                1040

Ser Ala Pro Thr Ala Asp Asn Asp Thr Asn Lys Ile Ala Glu Ala Phe
                1045                1050                1055

Asn Arg Ile Gly Arg Phe Lys Ser Trp Val Lys Arg Asn Ile Ala Asp
                1060                1065                1070

Cys Phe Lys Leu Ile Arg Asn Lys Leu Thr Asn Gln Ile Ser Asp Gln
                1075                1080                1085

Pro Ser Glu His Gly Asp Asn Glu Leu Glu Leu Gly His Asp Glu Ile
                1090                1095                1100

Leu Ala Asp Gly Leu Ile Lys Lys Gly Ile Lys Glu Gln Thr Gln Leu
1105                1110                1115                1120

Glu Val Ala Ile Gly Asp Gly Met Glu Phe Thr Ile His Gly Asp Met
                1125                1130                1135

Lys Asn Asn Lys Pro Lys Lys Ser Lys Tyr Leu Asn Asn Ala Thr Asp
                1140                1145                1150

Asp Asp Thr Ala Ser Ile Asn Ser Tyr Gly Ser His Lys Asn Arg Pro
                1155                1160                1165

Phe Lys Asp Glu Ser His Lys Gly Ser Ala Glu Thr Met Glu Gly Glu
                1170                1175                1180

Glu Lys Arg Asp Ala Ser Lys Glu Asp Leu Gly Leu Asp Glu Glu Leu
1185                1190                1195                1200

Asp Glu Glu Gly Glu Cys Glu Glu Gly Pro Leu Asp Gly Asp Ile Ile
                1205                1210                1215

Ile His Ala His Asp Glu Asp Ile Leu Asp Glu Tyr Pro Ala Asp Cys
                1220                1225                1230

Cys Pro Asp Ser Tyr Tyr Lys Lys Phe Pro Ile Leu Ala Gly Asp Asp
                1235                1240                1245

Asp Ser Pro Phe Trp Gln Gly Trp Gly Asn Leu Arg Leu Lys Thr Phe
                1250                1255                1260

Arg Leu Ile Glu Asp Lys Tyr Phe Glu Thr Ala Val Ile Thr Met Ile
1265                1270                1275                1280
```

```
Leu Met Ser Ser Leu Ala Leu Ala Leu Glu Asp Val His Leu Pro Gln
            1285                1290                1295

Arg Pro Ile Leu Gln Asp Ile Leu Tyr Tyr Met Asp Arg Ile Phe Thr
            1300                1305                1310

Val Ile Phe Phe Leu Glu Met Leu Ile Lys Trp Leu Ala Leu Gly Phe
            1315                1320                1325

Lys Val Tyr Leu Thr Asn Ala Trp Cys Trp Leu Asp Phe Val Ile Val
            1330                1335                1340

Met Val Ser Leu Ile Asn Phe Val Ala Ser Leu Val Gly Ala Gly Gly
1345                1350                1355                1360

Ile Gln Ala Phe Lys Thr Met Arg Thr Leu Arg Ala Leu Arg Pro Leu
            1365                1370                1375

Arg Ala Met Ser Arg Met Gln Gly Met Arg Val Val Asn Ala Leu
            1380                1385                1390

Val Gln Ala Ile Pro Ser Ile Phe Asn Val Leu Leu Val Cys Leu Ile
            1395                1400                1405

Phe Trp Leu Ile Phe Ala Ile Met Gly Val Gln Leu Phe Ala Gly Lys
            1410                1415                1420

Tyr Phe Lys Cys Glu Asp Met Asn Gly Thr Lys Leu Ser His Glu Ile
1425                1430                1435                1440

Ile Pro Asn Arg Asn Ala Cys Glu Ser Glu Asn Tyr Thr Trp Val Asn
            1445                1450                1455

Ser Ala Met Asn Phe Asp His Val Gly Asn Ala Tyr Leu Cys Leu Phe
            1460                1465                1470

Gln Val Ala Thr Phe Lys Gly Trp Ile Gln Ile Met Asn Asp Ala Ile
            1475                1480                1485

Asp Ser Arg Glu Val Asp Lys Gln Pro Ile Arg Glu Thr Asn Ile Tyr
            1490                1495                1500

Met Tyr Leu Tyr Phe Val Phe Phe Ile Ile Phe Gly Ser Phe Phe Thr
1505                1510                1515                1520

Leu Asn Leu Phe Ile Gly Val Ile Ile Asp Asn Phe Asn Glu Gln Lys
            1525                1530                1535

Lys Lys Ala Gly Gly Ser Leu Glu Met Phe Met Thr Glu Asp Gln Lys
            1540                1545                1550

Lys Tyr Tyr Ser Ala Met Lys Lys Met Gly Ser Lys Pro Leu Lys
            1555                1560                1565

Ala Ile Pro Arg Pro Arg Trp Arg Pro Gln Ala Ile Val Phe Glu Ile
            1570                1575                1580

Val Thr Asp Lys Lys Phe Asp Ile Ile Ile Met Leu Phe Ile Gly Leu
1585                1590                1595                1600

Asn Met Phe Thr Met Thr Leu Asp Arg Tyr Asp Ala Ser Asp Thr Tyr
            1605                1610                1615

Asn Ala Val Leu Asp Tyr Leu Asn Ala Ile Phe Val Val Ile Phe Ser
            1620                1625                1630

Ser Glu Cys Leu Leu Lys Ile Phe Ala Leu Arg Tyr His Tyr Phe Ile
            1635                1640                1645

Glu Pro Trp Asn Leu Phe Asp Val Val Val Ile Leu Ser Ile Leu
            1650                1655                1660

Gly Leu Val Leu Ser Asp Ile Ile Glu Lys Tyr Phe Val Ser Pro Thr
1665                1670                1675                1680

Leu Leu Arg Val Val Arg Val Ala Lys Val Gly Arg Val Leu Arg Leu
            1685                1690                1695

Val Lys Gly Ala Lys Gly Ile Arg Thr Leu Leu Phe Ala Leu Ala Met
```

-continued

```
                 1700                1705                1710
Ser Leu Pro Ala Leu Phe Asn Ile Cys Leu Leu Phe Leu Val Met
            1715                1720                1725
Phe Ile Phe Ala Ile Phe Gly Met Ser Phe Met His Val Lys Glu
        1730                1735                1740
Lys Ser Gly Ile Asn Asp Val Tyr Asn Phe Lys Thr Phe Gly Gln Ser
1745                1750                1755                1760
Met Ile Leu Leu Phe Gln Met Ser Thr Ser Ala Gly Trp Asp Gly Val
                1765                1770                1775
Leu Asp Ala Ile Ile Asn Glu Glu Ala Cys Asp Pro Pro Asp Asn Asp
            1780                1785                1790
Lys Gly Tyr Pro Gly Asn Cys Gly Ser Ala Thr Val Gly Ile Thr Phe
        1795                1800                1805
Leu Leu Ser Tyr Leu Val Ile Ser Phe Leu Ile Val Ile Asn Met Tyr
    1810                1815                1820
Ile Ala Val Ile Leu Glu Asn Tyr Ser Gln Ala Thr Glu Asp Val Gln
1825                1830                1835                1840
Glu Gly Leu Thr Asp Asp Asp Tyr Asp Met Tyr Tyr Glu Ile Trp Gln
                1845                1850                1855
Gln Phe Asp Pro Glu Gly Thr Gln Tyr Ile Arg Tyr Asp Gln Leu Ser
            1860                1865                1870
Glu Phe Leu Asp Val Leu Glu Pro Pro Leu Gln Ile His Lys Pro Asn
        1875                1880                1885
Lys Tyr Lys Ile Ile Ser Met Asp Ile Pro Ile Cys Arg Gly Asp Leu
    1890                1895                1900
Met Tyr Cys Val Asp Ile Leu Asp Ala Leu Thr Lys Asp Phe Phe Ala
1905                1910                1915                1920
Arg Lys Gly Asn Pro Ile Glu Glu Thr Gly Glu Ile Gly Glu Ile Ala
                1925                1930                1935
Ala Arg Pro Asp Thr Glu Gly Tyr Glu Pro Val Ser Ser Thr Leu Trp
            1940                1945                1950
Arg Gln Arg Glu Glu Tyr Cys Ala Arg Leu Ile Gln His Ala Trp Arg
        1955                1960                1965
Lys His Lys Ala Arg Gly Glu Gly Gly Ser Phe Glu Pro Asp Thr
    1970                1975                1980
Asp His Gly Asp Gly Gly Asp Pro Asp Ala Gly Asp Pro Ala Pro Asp
1985                1990                1995                2000
Glu Ala Thr Asp Gly Asp Ala Pro Ala Gly Gly Asp Gly Ser Val Asn
                2005                2010                2015
Gly Thr Ala Glu Gly Ala Ala Asp Ala Asp Glu Ser Asn Val Asn Ser
            2020                2025                2030
Pro Gly Glu Asp Ala Ala Ala Ala Ala Ala Ala Ala Ala Ala Ala
        2035                2040                2045
Ala Ala Gly Thr Thr Thr Ala Gly Ser Pro Gly Ala Gly Ser Ala Gly
    2050                2055                2060
Arg Gln Thr Ala Val Leu Val Glu Ser Asp Gly Phe Val Thr Lys Asn
2065                2070                2075                2080
Gly His Lys Val Val Ile His Ser Arg Ser Pro Ser Ile Thr Ser Arg
                2085                2090                2095
Thr Ala Asp Val
            2100
```